United States Patent
Johnson et al.

(10) Patent No.: US 8,076,457 B2
(45) Date of Patent: *Dec. 13, 2011

(54) CRYSTAL OF A CYTOCHROME-LIGAND COMPLEX AND METHODS OF USE

(75) Inventors: Eric F. Johnson, Encinitas, CA (US); Jason K. Yano, Vista, CA (US)

(73) Assignee: The Scripps Research Institute, La Jolla, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/117,470

(22) Filed: May 27, 2011

(65) Prior Publication Data

US 2011/0229923 A1    Sep. 22, 2011

Related U.S. Application Data

(62) Division of application No. 11/445,018, filed on Jun. 1, 2006, now Pat. No. 7,953,557.

(60) Provisional application No. 60/686,948, filed on Jun. 1, 2005.

(51) Int. Cl.
G01N 33/48 (2006.01)
G01N 31/00 (2006.01)
G06G 7/58 (2006.01)
G01N 33/53 (2006.01)
C07K 1/00 (2006.01)

(52) U.S. Cl. ............. 530/350; 702/19; 702/27; 703/11; 435/7.71

(58) Field of Classification Search ........................ None
See application file for complete search history.

(56) References Cited

U.S. PATENT DOCUMENTS

2004/0106216 A1    6/2004  Matsui
2004/0137518 A1    7/2004  Lambert

OTHER PUBLICATIONS

Lewis et al. (Molecular modeling of the human cytochrome P450 isoform CYP2A6 and investigations of CYP2A substrate selectivity, Toxicology, 133, (1999), pp. 1-33).*
Branden et al., "Introduction to Protein Structure Second Edition", Garland Publishing Inc., New York, 1999.
Drenth et al., "Principles of X-ray Crystallography," Springer, New York, 1995.
Giege et al., "Crystallogenesis of Biological Macromolecules: Facts and Perspectives," Acta Cryst., 1994, D50: 339-350.
Kierzek et al., Biophys Chem, 2001, 91:1-20.
Koenigs et al., "Mechanism-based inactivation of P450 2A6 by furanocoumarins," Biochemistry, 1998, 37, 10047-10061.
Lewis et al., "Molecular modeling of the human cytochrome P450 isoform CYP2A6 and investigations of CYP2A substrate selectivity," Toxicology, 133, (1999), pp. 1-33.
Poso, Antti et al., "A comparative molecular field analysis of cytochrome P450 2A5 and 2A6 inhibitors," Journal of Computer-Aided Molecular Design (2001), 15 (3), 195-202.
Sellers, Edward et al., "Inhibition of cytochrome P450 2A6 increases nicotine's oral bioavailability and decreases smoking," Clinical Pharmacology & Therapeutics, pp. 35-43, Jul. 2000.
Turpeinen, Miia et al., "Selective inhibition of CYP2B6-catalyzed bupropion hydroxylation in human liver microsomes in vitro," Drug Metabolism and Disposition (2004), 32(6), 626-631.
Wiencek, Ann Rev Biomed Eng, 1999, 1:505-534.
Williams et al., "Crystal structure of human cytochrome P450 2C9 with bound warfarin," Nature, 2003, 424 (6947) pp. 464-468, Epub Jul. 13, 2003.
Yano, Jason K. et al., "Structures of human microsomal cytochrome P450 2A6 complexed with coumarin and methoxsalen," Nature Structural & Molecular Biology (2005), 12(9), 822-823.
Zhang, Wenjiang et al., "Evaluation of methoxsalen, tranylcypromine, and tryptamine as specific and selective CYP2A6 inhibitors in vitro," Drug Metabolism and Disposition (2001), 9(6), 897-902.

* cited by examiner

*Primary Examiner* — Suzanne M Noakes
*Assistant Examiner* — Jae W Lee
(74) *Attorney, Agent, or Firm* — RatnerPrestia

(57) ABSTRACT

The teachings relates to the three-dimensional structure of a crystal of a cytochrome protein complexed with a ligand. The three-dimensional structure of four cytochrome P450 2A6-ligand complexes are disclosed. Cytochrome P450 2A6-ligand crystal structures, wherein the ligand is an inhibitor molecule, are useful for providing structural information that may be integrated into drug screening and drug design processes. Thus, the teachings also relate to methods for utilizing a crystal structure of a cytochrome P450 2A6-ligand complex for identifying, designing, selecting, or testing inhibitors of the cytochrome protein. Such inhibitors are useful as therapeutics for the treatment or modulation of i) diseases; ii) disease symptoms; or iii) the effect of other physiological events mediated by the cytochrome.

10 Claims, 12 Drawing Sheets

CRYSTAL OF A CYTOCHROME-LIGAND COMPLEX AND METHODS OF USE

CROSS-REFERENCE TO RELATED APPLICATIONS

Figure 1:
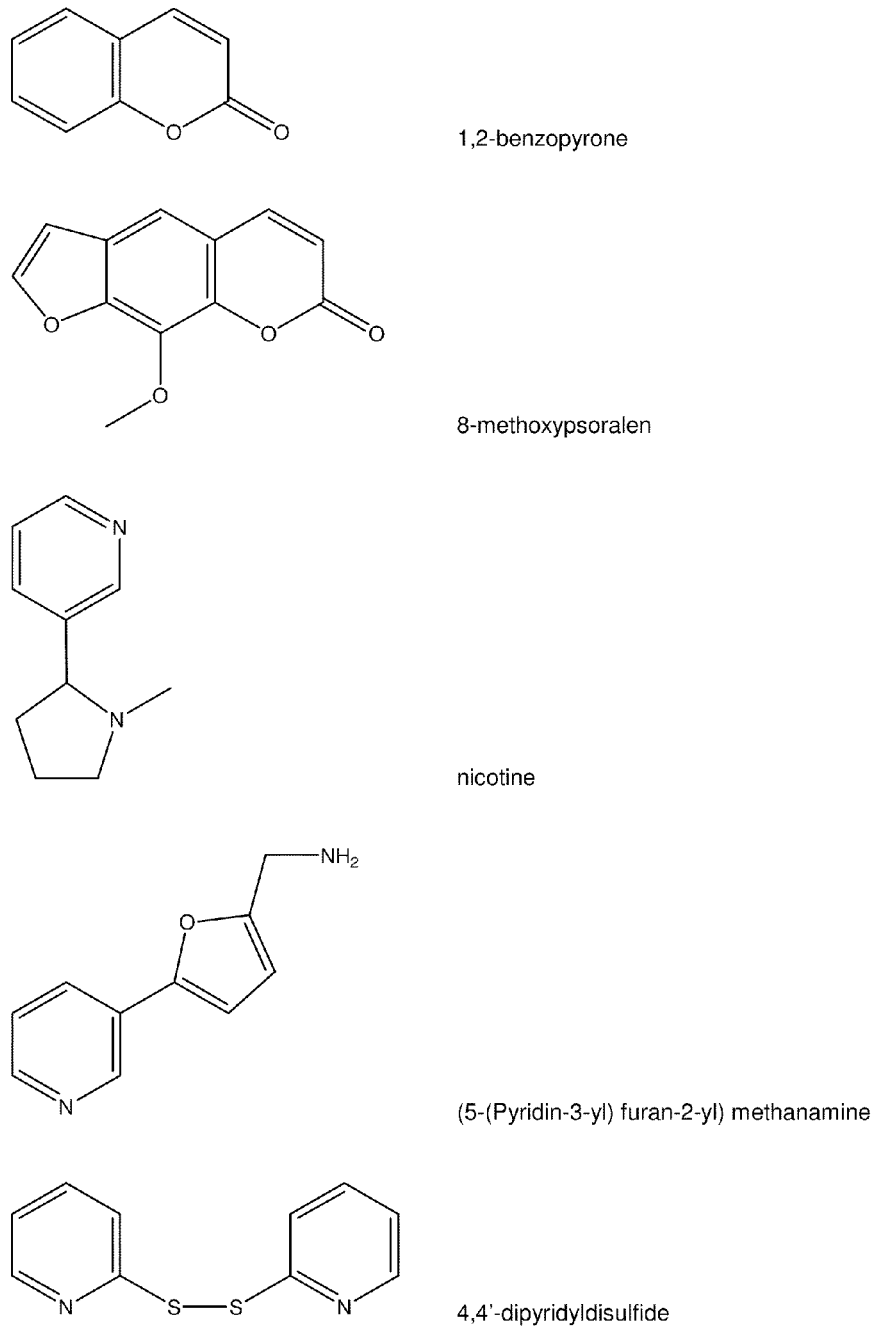

This application is a Divisional of U.S. application Ser. No. 11/445,018 filed on Jun. 1, 2006, which claims priority from U.S. Provisional Application Ser. No. 60/686,948 filed on Jun. 1, 2005, which are both incorporated herein by reference in their entirety.

STATEMENT REGARDING FEDERALLY SPONSORED RESEARCH OR DEVELOPMENT

This invention was made with Government support under Contract Nos. GM031001 and RR00833 awarded by the National Institutes of Health. The Government has certain rights in this invention.

INCORPORATION-BY-REFERENCE OF MATERIAL SUBMITTED ON A COMPACT DISC

The Compact Disc Appendix (CD Appendix), which is a part of the present disclosure, includes one folder designated CD Appendix on the compact disc. The CD Appendix contains "Table 1.DOC" having 254 pages and a size of 2925 KB, "Table 2.DOC" having 257 pages and a size of 2971 KB, "Table 3.DOC" having 154 pages and a size of 1461 KB, "Table 4.DOC" having 258 pages and a size of 1856 KB, and "Table 5.DOC" having 258 pages and a size of 1854 KB, each table having over 50 pages, of the present invention comprising the atomic coordinates of exemplary crystal structures. A portion of the disclosure of this patent document contains material which is subject to copyright protection. The copyright owner of that material has no objection to the facsimile reproduction by anyone of the patent document or the patent disclosure, as it appears in the Patent and Trademark Office patent files or records, but otherwise reserves all copyright. The subject matter of the CD Appendix is incorporated herein by reference in its entirety.

The Sequence Listing, which is a part of the present disclosure, includes a computer readable form and a written sequence listing comprising nucleotide and amino acid sequences of the present invention. The sequence listing information recorded in computer readable form is identical to the written sequence listing. The subject matter of the Sequence Listing is incorporated herein by reference in its entirety.

FIELD

The present invention relates to three dimensional structures and models of cytochrome P450 2A6 complexed with various ligands, and uses thereof.

INTRODUCTION

Human cytochrome P450 2A6, a xenobiotic-metabolizing P450 monooxygenase, is the primary enzyme responsible for nicotine detoxification. Nicotine (FIG. 1) is the primary addictive agent in tobacco products that contributes to the establishment and maintenance of tobacco dependence. Individual variation in cytochrome P450 2A6-mediated nicotine metabolism resulting from allelic differences can alter nicotine bioavailability and affect smoking behavior. Additionally, treatment of volunteers with the cytochrome P450 2A6 inhibitor methoxsalen (8-methoxypsoralen, FIG. 1) increases oral availability of nicotine and decreases smoking.

Cytochrome P450 2A6 oxidizes a number of relatively small substrate molecules, including pharmaceutical compounds such as coumarin (1,2-benzopyrone, FIG. 1), which is selectively oxidized to a 7-hydroxylated product, umbelliferone; (+)-cis-3,5-dimethyl-2-(3-pyridyl)thiazolidin-4-one hydrochloride (SM-12502); fadrozole; and losigamone. Additionally, cytochrome P450 2A6 catalyzes the conversion of the prodrug Tegafur to the antineoplastic agent, 5-fluorouracil.

Cytochrome P450 2A6 also activates tobacco-specific carcinogens such as (NNN)N'-nitrosonornicotine 4 and 4-(methylnitrosamino)-1-(3pyridyl)-1-butanone (NNK), converting them to mutagenic products. A recent study in the Japanese population demonstrated that individuals having at least one of several alleles encoding cytochrome P450 2A6 with diminished activity exhibited a significantly lower incidence of tobacco-related lung cancer. This effect was most pronounced in individuals who were homozygous for the 2A6*4 deletion allele. Additionally, an in vivo study demonstrated that inhibition of cytochrome P450 2A6 activity using the inhibitor methoxsalen allows nicotine levels to remain elevated while significantly more NNK is metabolized to an inactive NNAL glucuronide conjugate.

Diminished cytochrome P450 2A6 activity appears to correlate with a decrease in tobacco-related lung cancer without causing apparent adverse effects on drug metabolism. However, a detailed view of related conformational changes has remained unsolved. Thus, the development of useful reagents for treatment or diagnosis of disease has been hindered by lack of structural information of cytochrome P450s, and in particular cytochrome-ligand complexes. Therefore, there is a need in the art to elucidate the three dimensional structure and models of cytochrome-ligand complexes, and to use such structures and models in therapeutic strategies, such as drug design.

SUMMARY

Accordingly, the present inventors have developed methods for designing drugs which reduce inactivation rates of pharmaceutically active compounds which are inactivated by a cytochrome P450 such as a cytochrome P450 2A6. Similarly, the present inventors have developed methods for inhibiting activation of at least one procarcinogen. These methods, in various configurations, comprise selecting an inhibitor of cytochrome P450 2A6 by performing a structure based drug design using a three-dimensional structure determined for a crystal comprising cytochrome P450 2A6 complexed with a cytochrome P450 2A6 ligand; and contacting a sample or a subject comprising cytochrome P450 2A6 with the inhibitor. A subject can be, in some configurations, a human subject in need of treatment wherein the treatment involves reduction of inactivation rate of a pharmaceutically active compound, inhibiting activation of at least one procarcinogen, or a combination thereof. Furthermore, in various aspects, the contacting the subject with the inhibitor can comprise administering the inhibitor to the human subject. Some examples of pharmaceutically active compounds for which inactivation can be inhibited include, without limitation, 1,2-benzopyrone, halothane, letrozole, losigamone, (+)-cis-3,5-dimethyl-2-(3-pyridyl) thiazolidin-4-one hydrochloride (SM-12502), valproic acid, disulfuram, and 8-methoxypsoralen. Examples of procarcinogens whose activation can be inhibited include, without limitation, certain tobacco procarcinogens such as N'-nitrosonornicotine (NNN) and 4-(methylnitrosamino)-1-(3-pyridyl)-1-butanone (NNK).

In various configurations of the present teachings, the cytochrome P450 2A6 ligand comprised by a crystal can be a psoralen, such as 8-methoxypsoralen (methoxsalen). In certain alternative configurations, the ligand can be a coumarin, such as 1,2-benzopyrone. In addition, the selecting can comprise a) performing a structure-based drug design using a three-dimensional structure determined for a crystal of the cytochrome P450 2A6 to identify a candidate inhibitor; b) contacting the candidate inhibitor with a cytochrome P450 2A6; and c) detecting inhibition of at least one activity of the cytochrome P450 2A6. In various aspects of the present teachings, a cytochrome P450 2A6 can be a human cytochrome P450 2A6. In addition, in some configurations, a cytochrome P450 2A6 inhibitor can be an antibody directed against cytochrome P450 2A6, such as a monoclonal antibody directed against cytochrome P450 2A6.

In various aspects of the present teachings, the inventors have developed methods for designing a drug which interferes with an activity of a cytochrome P450 2A6. These methods comprise (a) providing on a digital computer a three-dimensional structure of a cytochrome P450 2A6-ligand complex comprising the cytochrome P450 2A6 and a ligand of the cytochrome P450 2A6; and (b) using software comprised by the digital computer to design a chemical compound which is predicted to bind to the cytochrome P450 2A6. These methods can further comprise (c) synthesizing or obtaining the chemical compound; and (d) evaluating the chemical compound for an ability to interfere with an activity of the cytochrome P450 2A6. In some configurations, the methods can further include using software comprised by the digital computer to design a chemical compound which not only is predicted to bind to cytochrome P450 2A6, but is also predicted not to bind to other cytochrome P450 proteins, such as, for example, cytochrome P450 2C8, cytochrome P450 2C9, and/or cytochrome P450 3A4.

In various configurations of these aspects, a cytochrome P450 2A6 can consist of an amino acid sequence as set forth in SEQ ID NO: 2, can consist essentially of an amino acid sequence as set forth in SEQ ID NO: 2, or can comprise an amino acid sequence as set forth in SEQ ID NO: 2. In various alternative configurations of these aspects, a cytochrome P450 2A6 can consist of an amino acid sequence as set forth in SEQ ID NO: 3, can consist essentially of an amino acid sequence as set forth in SEQ ID NO: 3, or can comprise an amino acid sequence as set forth in SEQ ID NO: 3.

In these aspects, a cytochrome P450 2A6 ligand can be a psoralen such as 8-methoxypsoralen, or a coumarin such as 1,2-benzopyrone. In addition, a cytochrome P450 2A6 ligand can be (5-(Pyridin-3-yl) furan-2-yl)methanamine or 4,4'-dipyridyldisulfide (Aldrithiol™). Furthermore, in these aspects, a chemical compound can be designed by computational interaction with reference to a three dimensional site of the structure of the cytochrome P450 2A6-ligand complex, wherein the three dimensional site comprises an amino acid selected from the group consisting of Phe107, Phe111, Phe118, Phe209, Phe480, Val117, Asn297, Ile 300, Gly301, Thr305, Ile366, Leu370 and a combination thereof.

In certain aspects of the present teachings, the present inventors have developed methods for generating a model of a three dimensional structure of a cytochrome P450 2A6-ligand complex. In these aspects, a method can comprise (a) providing an amino acid sequence of a reference cytochrome P450 family 2 polypeptide and an amino acid sequence of a target cytochrome P450 2A6 comprised by the cytochrome P450 2A6-ligand complex; (b) identifying structurally conserved regions shared between the reference cytochrome P450 family 2 amino acid sequence and the target cytochrome P450 2A6 amino acid sequence; and (c) assigning atomic coordinates from the conserved regions to the target cytochrome P450 2A6-ligand complex. The amino acid sequence of a cytochrome P450 2A6 in these aspects can be as described above. In these aspects, a target cytochrome P450 2A6-ligand complex can have a three dimensional structure described by atomic coordinates which substantially conform to atomic coordinates set forth in Table 1 (describing coordinates of a cytochrome P450 2A6 complexed with 8-methoxypsoralen) or in Table 2 (describing coordinates of a cytochrome P450 2A6 complexed with 1,2-benzopyrone). Additionally, a reference cytochrome P450 can be, in some configurations, a cytochrome P450 2C8 having a three dimensional structure described by atomic coordinates that substantially conform to atomic coordinates set forth in Table 3. In addition, a target cytochrome P450 2A6-ligand complex can have a three dimensional structure described by atomic coordinates which substantially conform to atomic coordinates set forth in Table 4 (describing coordinates of a cytochrome P450 2A6 complexed with (5-(Pyridin-3-yl) furan-2-yl)methanamine) or in Table 5 (describing coordinates of a cytochrome P450 2A6 complexed with 4,4'-dipyridyldisulfide).

In certain aspects of the present teachings, the present inventors have developed methods for determining a three dimensional structure of a target cytochrome P450 2A6-ligand complex. In various configurations of these aspects, a method can comprise (a) providing an amino acid sequence of a target cytochrome P450 2A6 (b) predicting the pattern of folding of the amino acid sequence in a three dimensional conformation using a fold recognition algorithm; and (c) comparing the pattern of folding of the target structure amino acid sequence with the three dimensional structure of a known cytochrome P450 family 2 polypeptide-ligand complex. The amino acid sequence of a target cytochrome P450 2A6 in these aspects can be as described above, and a known cytochrome P450 family 2 polypeptide-ligand complex can comprise a three dimensional structure described by atomic coordinates that substantially conform to atomic coordinates of cytochrome P450 2C8 as set forth in Table 3, or can be an amino acid sequence of a polypeptide selected from the group consisting of cytochrome P450 2C8, cytochrome P450 2A7 and cytochrome P450 2A13.

In various aspects of the present teachings, the present inventors disclose a crystal comprising a cytochrome P450 2A6 and a cytochrome P450 2A6 ligand. In certain configurations of these aspects, a cytochrome P450 2A6 ligand can be a psoralen such as 8-methoxypsoralen, and a crystal can comprise a space group $P2_1$ so as to form a unit cell of dimensions a=70.66 Å, b=159.03 Å, c=103.88 Å, and β=92.00. In an alternative configuration, a cytochrome P450 2A6 ligand can be a coumarin such as 1,2-benzopyrone, and a crystal can comprise a space group $P2_1$ so as to form a unit cell of dimensions a=70.62 Å, b=157.59 Å, c=103.54 Å, and β=92.25.

In other aspects of the present teachings, the inventors have developed a crystal comprising cytochrome P450 2A6 complexed with a cytochrome P450 2A6 ligand, wherein the crystal is sufficiently pure to determine atomic coordinates of the complex by X-ray diffraction to a resolution of about 2.05 Å. In some configurations of these aspects, the cytochrome P450 2A6 ligand can be 8-methoxypsoralen, 1,2-benzopyrone, (5-(Pyridin-3-yl) furan-2-yl)methanamine), or 4,4'-dipyridyldisulfide. In alternative configurations, the crystal can be sufficiently pure to determine atomic coordinates of the complex by X-ray diffraction to a resolution of about 1.90 Å. In some configurations of these aspects, the cytochrome P450 2A6 ligand can be 8-methoxypsoralen, 1,2-benzopyrone, (5-(Pyridin-3-yl) furan-2-yl)methanamine), or 4,4'-dipyridyldisulfide.

In some aspects of the present disclosure, the invention includes a therapeutic compound which inhibits tobacco carcinogen activation by cytochrome P450 2A6. In these aspects, a compound can be selected by a) performing a structure based drug design using a three-dimensional structure determined for a crystal comprising cytochrome P450 2A6 and a cytochrome P450 2A6 ligand, b) contacting a sample comprising cytochrome P450 2A6 with the compound, and c) detecting inhibition of at least one activity of the cytochrome P450 2A6. In some aspects, the activity of the cytochrome P450 2A6 can be activation of a tobacco carcinogen.

Certain aspects of the present teachings include a three dimensional computer image of the three dimensional structure of a cytochrome P450 2A6-ligand complex. In these aspects, a structure can substantially conform with the three dimensional coordinates listed in Table 1, Table 2, Table 4 or Table 5.

Certain aspects of the present teachings include a computer-readable medium encoded with a set of three dimensional coordinates as set forth in Table 1, Table 2, Table 4 or Table 5. In these aspects, the three dimensional coordinates set forth in Table 1, Table 2, Table 4 or Table 5 can be used in conjunction with a graphical display software program to create an electronic file that can be visualized on a computer capable of representing the electronic file as a three dimensional image.

Certain aspects of the present teachings include a computer-readable medium encoded with a set of three dimensional coordinates of a three dimensional structure which substantially conforms to the three dimensional coordinates represented in Table 1, Table 2, Table 4 or Table 5. In these aspects, using a graphical display software program, the set of three dimensional coordinates can be used to create an electronic file that can be visualized on a computer capable of representing said electronic file as a three dimensional image.

Some aspects of the present teachings disclose methods of forming a crystal comprising a cytochrome P450 2A subfamily member and a ligand of the cytochrome P450 2A subfamily member ligand. In various configurations, these methods can comprise forming a composition comprising the cytochrome P450 2A subfamily member, the ligand, water and a non-ionic detergent; and adding a solution comprising ammonium sulfate and a polyethylene glycol to the composition. In various configurations, the non-ionic detergent can be a polyoxyethylene non-ionic detergent, such as, without limitation, ANAPOE®-X-405 non-ionic detergent. In various aspects, the cytochrome P450 2A subfamily member can be a cytochrome P450 2A6 and the cytochrome P450 2A subfamily member ligand can be a cytochrome P450 2A6 ligand. As described above, a ligand in these configurations can be a psoralen such as 8-methoxypsoralen, or a coumarin such as 1,2-benzopyrone.

In various aspects of the present teachings, the inventors have developed methods for promoting cessation of tobacco smoking. Methods of these aspects can comprise selecting an inhibitor of cytochrome P450 2A6 by performing a structure based drug design using a three-dimensional structure determined for a crystal comprising the cytochrome P450 2A6 and a cytochrome P450 2A6 ligand such as those described above, and administering an effective amount of the inhibitor to a human individual in need thereof. In various aspects, a method can further comprise administering nicotine to the individual. The administering nicotine can comprise administering nicotine to the individual orally. In various aspects, a method can further comprise a method for inhibiting activation of at least one tobacco procarcinogen. In these aspects, the administering an effective amount of the inhibitor can comprise administering an amount effective for both promoting cessation of tobacco smoking and inhibiting activation of at least one tobacco procarcinogen. In addition, in some configurations, the tobacco procarcinogen can be a carcinogen which can be activated by cytochrome P450 2A6, such as N'-nitrosonornicotine (NNN), 4-(methylnitrosamino)-1-(3pyridyl)-1-butanone (NNK) or a combination thereof. In certain aspects, the selecting can comprise a) performing a structure-based drug design using a three-dimensional structure determined for a crystal of the cytochrome P450 2A6 to identify a candidate inhibitor, b) contacting the candidate inhibitor with a cytochrome P450 2A6, and c) detecting inhibition of at least one activity of the cytochrome P450 2A6. Furthermore, in these and the other aspects described herein, the cytochrome P450 2A6 can be a human cytochrome P450 2A6.

These and other features, aspects and advantages of the present teachings will become better understood with reference to the following description, examples and appended claims.

DRAWINGS

FIG. 1. Chemical structures of CYP2A6 ligands 1,2-benzopyrone, 8-methoxypsoralen, nicotine, (5-(Pyridin-3-yl) furan-2-yl)methanamine, and 4,4'-dipyridyldisulfide.

Figure 2:
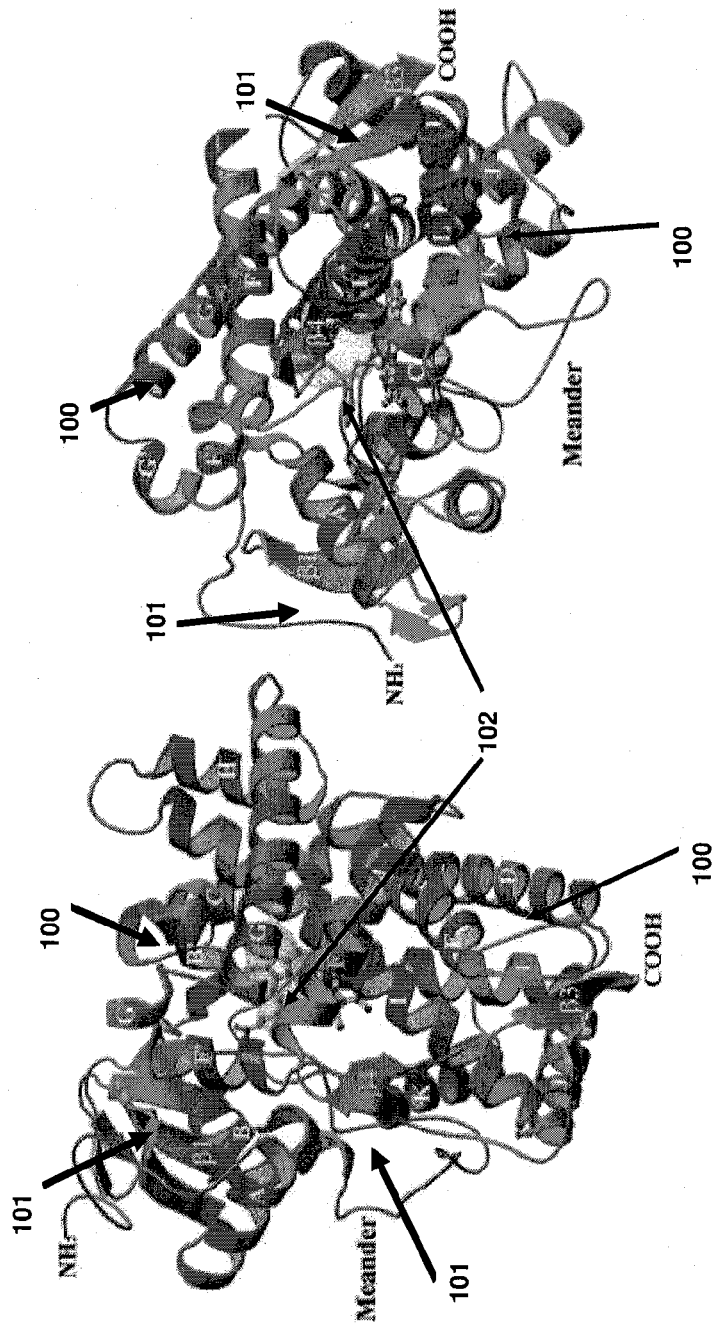

FIG. 2. Two views of the overall fold of CYP2A6 (left) and cytochrome P450 2C8 (right).

Figure 3:
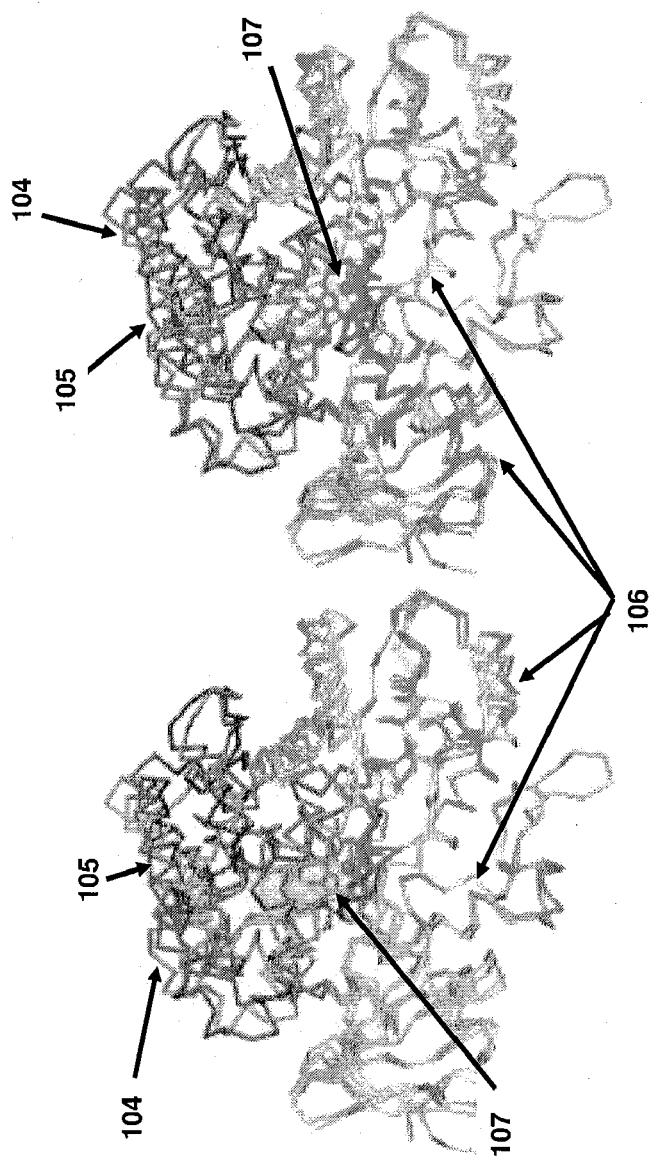

FIG. 3. Two views of Cα trace overlays of CYP2A6 (left) and cytochrome P450 2C8 (right).

Figure 4:
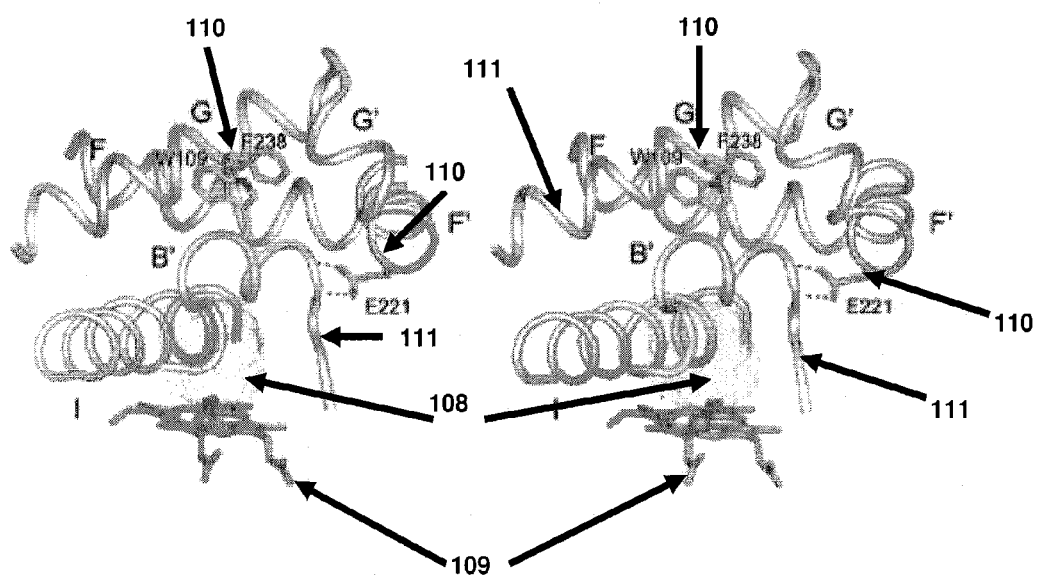

FIG. 4. Two wall-eyed stereo views of stabilizing interactions between CYP2A6 helix B' and the helix F' to helix G region.

Figure 5:
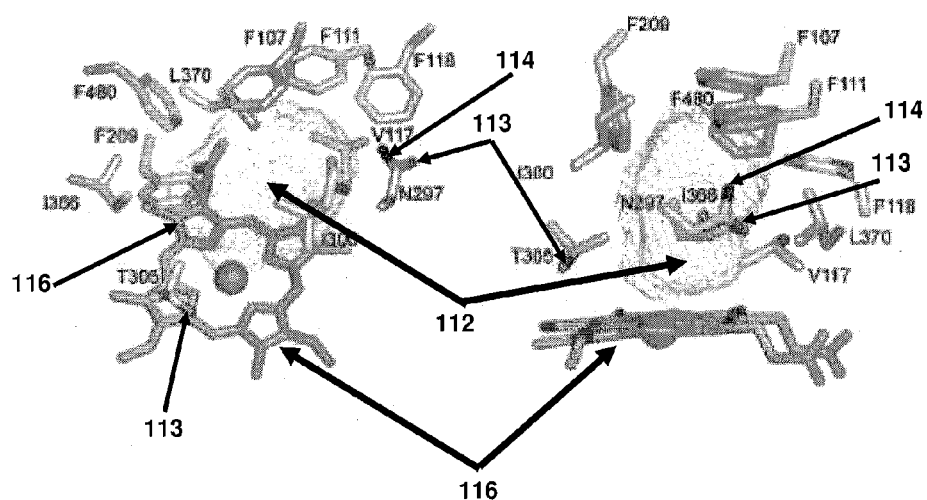

FIG. 5. Two views of the CYP2A6 active site cavity.

Figure 6:
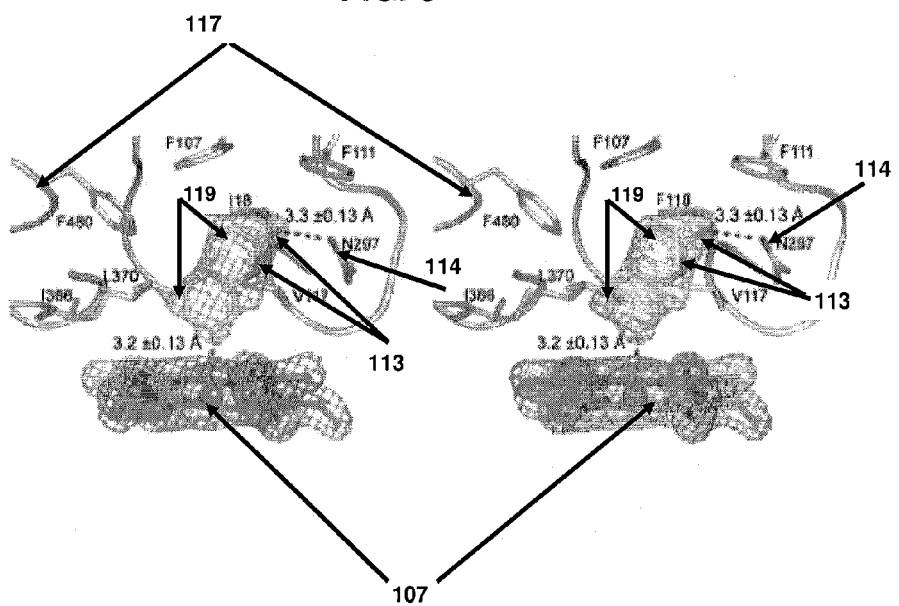

FIG. 6. Wall-eyed stereo view of σA weighted 2|Fo|-|Fc| composite omit electron density map of the heme and coumarin.

Figure 7:
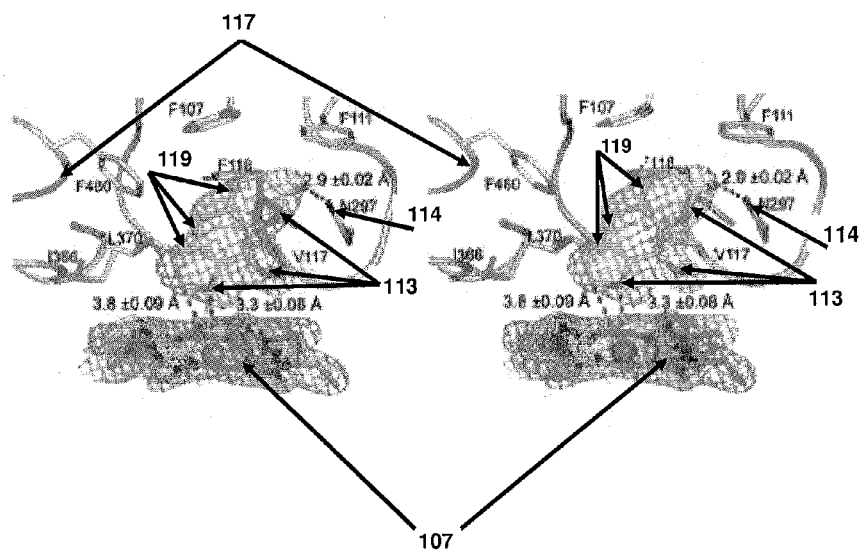

FIG. 7. Two wall-eyed stereo views of σA weighted 2|Fo|-|Fc| composite omit electron density maps of the heme and methoxsalen.

Figure 8:
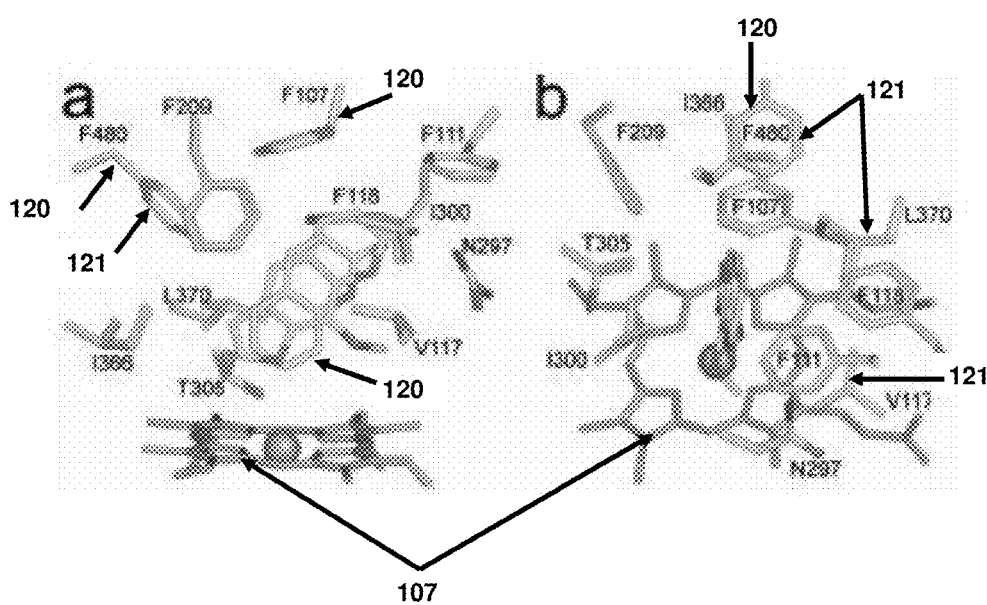

FIG. 8. Two views showing the superposed structures of the coumarin (a) and methoxsalen (b) complexes of CYP2A6.

Figure 9:
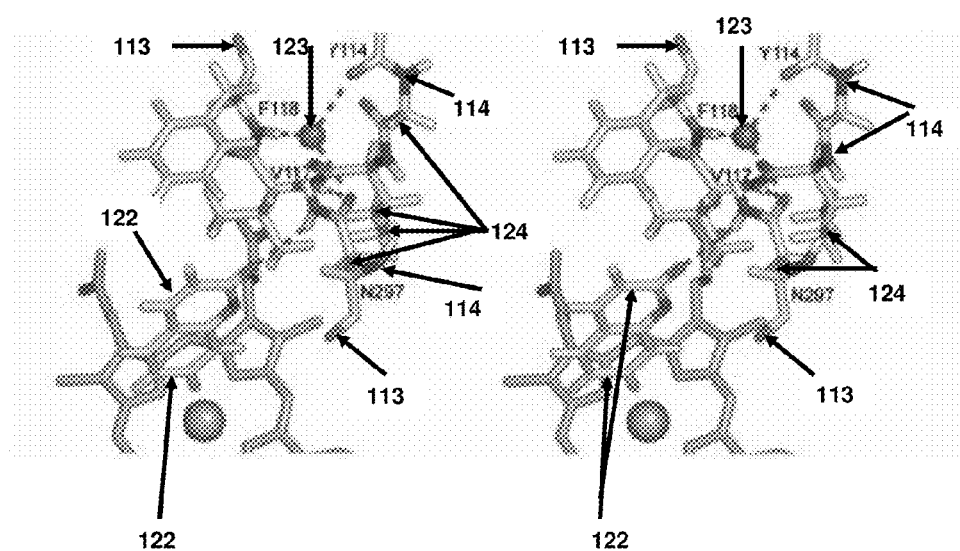

FIG. 9. Two wall-eyed stereo views of the potential hydrogen bonding of Asn297 with coumarin, the polypeptide chain and a conserved water molecule bound in a turn following helix B'.

Figure 10:
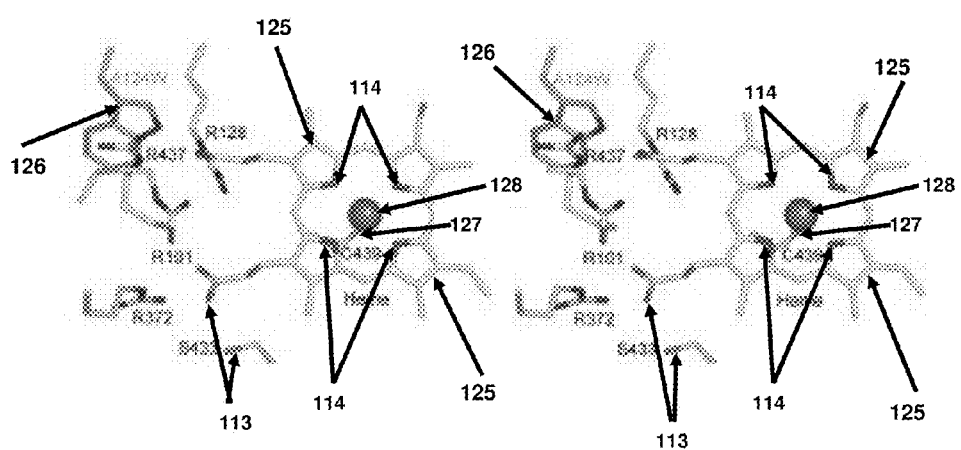

FIG. 10. Two wall-eyed stereo views of interactions between cytochrome P450 2A6 and the heme prosthetic group.

Figure 11:
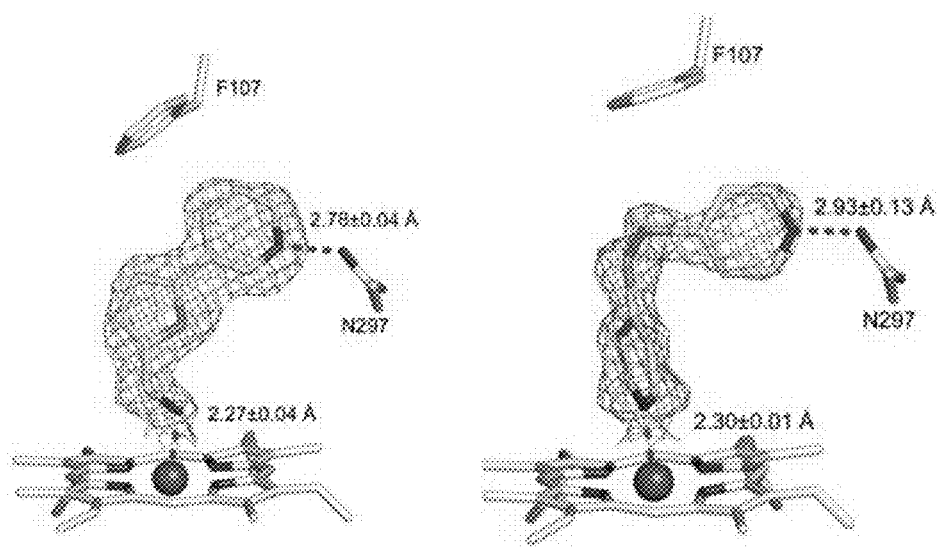

FIG. 11. σA weighted 2|Fo|-|Fc| omit electron density maps contoured at 1 σ and rendered within 1.5 Å of the ligand for the complexes of CYP2A6 with (5-(Pyridin-3-yl) furan-2-yl)methanamine (left) and 4,4'-dipyridyldisulfide (ALDRITHIOL™) (right) bound in the active site.

Figure 12:
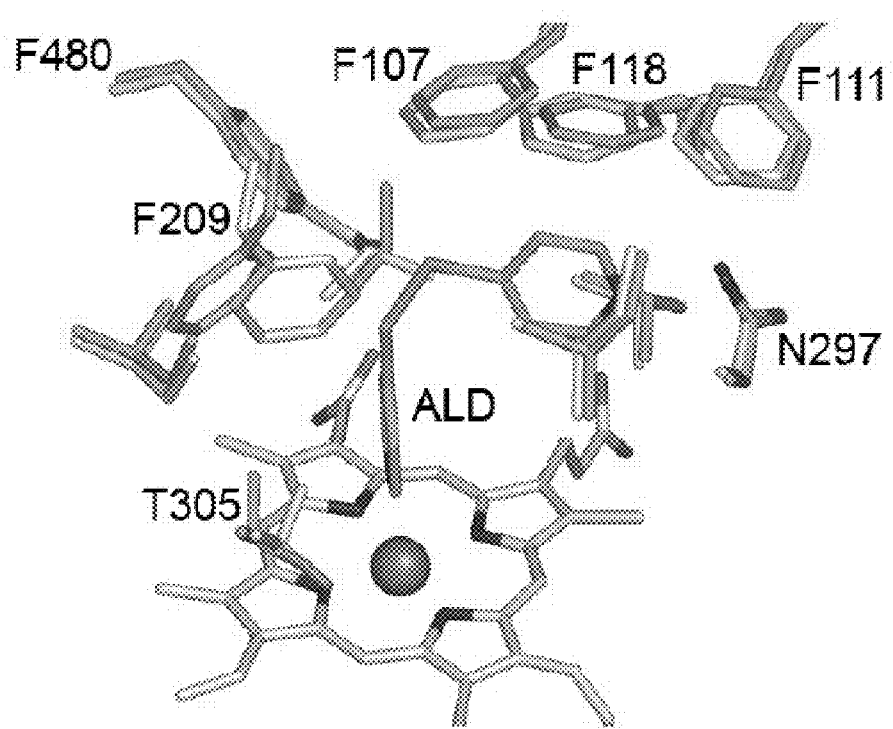

FIG. 12. 4,4'-dipyridyldisulfide (ALDRITHIOL™ (ALD)) interactions with CYP2A6.

DETAILED DESCRIPTION

The present teachings relate to the discovery of three-dimensional structures of cytochrome P450 2A6

("CYP2A6"; human sequence having SEQ ID NO: 1) complexed with various ligands (each complex individually referred to as a "cytochrome P450 2A6-ligand complex" or a "Cytochrome-Ligand Complex"), models of such three-dimensional structures, a method of structure-based drug design using such structures, the compounds identified by such methods and the use of such compounds in therapeutic compositions. In particular, the present teachings relate to a novel crystal of CYP2A6 complexed with ligands coumarin, methoxsalen, (5-(pyridin-3-yl) furan-2-yl)methanamine, and 4,4'-dipyridyldisulfide; methods of production of such crystals; three dimensional coordinates of such CYP2A6-ligand complexes; three dimensional structures of the CYP2A6-ligand complexes; and uses of such structure and models to derive other Cytochrome-Ligand Complex structures and in drug design strategies.

One aspect of the present teachings includes a model of a Cytochrome-Ligand Complex in which the model represents a three dimensional structure of a Cytochrome-Ligand Complex. Another aspect of the present teachings includes the three dimensional structure of a Cytochrome-Ligand Complex, such as the three dimensional structure of a Cytochrome-Ligand Complex which substantially conforms with the atomic coordinates represented in Table 1, Table 2, Table 4 or Table 5, corresponding to a CYP2A6-methoxsalen complex, a CYP2A6-coumarin complex, a CYP2A6-(5-(pyridin-3-yl) furan-2-yl)methanamine) complex, and a CYP2A6-(4, 4'-dipyridyldisulfide) complex respectfully. In to the present teachings, the term "substantially conforms" refers to at least a portion of a three dimensional structure of a Cytochrome-Ligand Complex which is sufficiently spatially similar to at least a portion of a specified three dimensional configuration of a particular set of atomic coordinates (e.g., those represented by Table 1, Table 2, Table 4 or Table 5) to allow the three dimensional structure of a Cytochrome-Ligand Complex to be modeled or calculated using the particular set of atomic coordinates as a basis for determining the atomic coordinates defining the three dimensional configuration of a Cytochrome-Ligand Complex.

More particularly, a structure that substantially conforms to a given set of atomic coordinates is a structure wherein at least about 50% of such structure has an average root-mean-square deviation (RMSD) of less than about 1.8 Å for the backbone atoms in secondary structure elements in each domain, and in various aspects, less than about 1.25 Å for the backbone atoms in secondary structure elements in each domain, and, in various aspects less than about 1.0 Å, in other aspects less than about 0.75 Å, less than about 0.5 Å, and, less than about 0.25 Å for the backbone atoms in secondary structure elements in each domain. In one aspect of the present teachings, a structure that substantially conforms to a given set of atomic coordinates is a structure wherein at least about 75% of such structure has the recited average RMSD value, and in some aspects, at least about 90% of such structure has the recited average RMSD value, and in some aspects, about 100% of such structure has the recited average RMSD value. In particular, the above definition of "substantially conforms" can be extended to include atoms of amino acid side chains. As used herein, the phrase "common amino acid side chains" refers to amino acid side chains that are common to both the structure which substantially conforms to a given set of atomic coordinates and the structure that is actually represented by such atomic coordinates.

In another aspect of the present teachings, a three dimensional structure that substantially conforms to a given set of atomic coordinates is a structure wherein at least about 50% of the common amino acid side chains have an average RMSD of less than about 1.8 Å, and in various aspects, less than about 1.25 Å, and, in other aspects, less than about 1.0 Å, less than about 0.75 Å, less than about 0.5 Å, and less than about 0.25 Å. In one aspect of the present teachings, a structure that substantially conforms to a given set of atomic coordinates is a structure wherein at least about 75% of the common amino acid side chains have the recited average RMSD value, and in some aspects, at least about 90% of the common amino acid side chains have the recited average RMSD value, and in some aspects, about 100% of the common amino acid side chains have the recited average RMSD value.

A three dimensional structure of a Cytochrome-Ligand Complex which substantially conforms to a specified set of atomic coordinates can be modeled by a suitable modeling computer program such as MODELER (A. Sali and T. L. Blundell, J. Mol. Biol., vol. 234:779-815, 1993 as implemented in the INSIGHT II® software package INSIGHT II®, available from ACCELERYS® (San Diego, Calif.)) and those software packages listed in the Examples, using information, for example, derived from the following data: (1) the amino acid sequence of the Cytochrome-Ligand Complex; (2) the amino acid sequence of the related portion(s) of the protein represented by the specified set of atomic coordinates having a three dimensional configuration; and, (3) the atomic coordinates of the specified three dimensional configuration. A three dimensional structure of a Cytochrome-Ligand Complex which substantially conforms to a specified set of atomic coordinates can also be calculated by a method such as molecular replacement, which is described in detail below.

A suitable three dimensional structure of the Cytochrome-Ligand Complex for use in modeling or calculating the three dimensional structure of another Cytochrome-Ligand Complex comprises the set of atomic coordinates represented in Table 1, Table 2, Table 4 or Table 5. The set of three dimensional coordinates set forth in Table 1, Table 2, Table 4 and Table 5 are represented in standard Protein Data Bank format. According to the present teachings, a Cytochrome-Ligand Complex has a three dimensional structure which substantially conforms to the set of atomic coordinates represented by Table 1, Table 2, Table 4 and/or Table 5. As used herein, a three dimensional structure can also be a most probable, or significant, fit with a set of atomic coordinates. According to the present teachings, a most probable or significant fit refers to the fit that a particular Cytochrome-Ligand Complex has with a set of atomic coordinates derived from that particular Cytochrome-Ligand Complex. Such atomic coordinates can be derived, for example, from the crystal structure of the protein such as the coordinates determined for the Cytochrome-Ligand Complex structure provided herein, or from a model of the structure of the protein. For example, the three dimensional structure of a monomeric or multimeric protein, including a naturally occurring or recombinantly produced cytochrome P450 protein, substantially conforms to and is a most probable fit, or significant fit, with the atomic coordinates of Table 1, Table 2, Table 4 and/or Table 5. The three dimensional crystal structure of the Cytochrome-Ligand Complex may comprise the atomic coordinates of Table 1, Table 2, Table 4 or Table 5. Also as an example, the three dimensional structure of another Cytochrome-Ligand Complex would be understood by one of skill in the art to substantially conform to the atomic coordinates of Table 1, Table 2, Table 4 and/or Table 5. This definition can be applied to the other cytochrome P450 proteins in a similar manner.

In various aspects of the present teachings, a structure of a Cytochrome-Ligand Complex substantially conforms to the atomic coordinates represented in Table 1, Table 2, Table 4 and/or Table 5. Such values as listed in Table 1, Table 2, Table 4 and/or Table 5 can be interpreted by one of skill in the art. In other aspects, a three dimensional structure of a Cytochrome-Ligand Complex substantially conforms to the three dimensional coordinates represented in Table 1, Table 2, Table 4 and/or Table 5. In other aspects, a three dimensional structure of a Cytochrome-Ligand Complex is a most probable fit with the three dimensional coordinates represented in Table 1, Table 2, Table 4 and/or Table 5. Methods to determine a substantially conforming and probable fit are within the expertise of skill in the art and are described herein in the Examples section.

A Cytochrome-Ligand Complex that has a three dimensional structure which substantially conforms to the atomic coordinates represented by Table 1, Table 2, Table 4 or Table 5 includes an cytochrome P450 protein having an amino acid sequence that is at least about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence of a eukaryotic CYP2A6 protein, in particular an amino acid sequence having SEQ ID NO: 2 or SEQ ID NO: 3, across the full-length of the CYP2A6 protein sequence. A sequence alignment program such as BLAST (available from the National Institutes of Health Internet web site) may be used by one of skill in the art to compare sequences of CYP2A6 protein to other cytochrome P450 proteins.

A three dimensional structure of any Cytochrome-Ligand Complex can be modeled using methods generally known in the art based on information obtained from analysis of a Cytochrome-Ligand Complex crystal, and from other Cytochrome-Ligand Complex structures which are derived from a Cytochrome-Ligand Complex crystal. The Examples section below discloses the production of a Cytochrome-Ligand Complex crystal, in particular CYP2A6 complexed with coumarin, CYP2A6 complexed with methoxsalen, CYP2A6 complexed with (5-(pyridin-3-yl)furan-2-yl)methanamine, CYP2A6 complexed with 4,4'-dipyridyldisulfide, as well as a model of a cytochrome P450 2A-ligand complex, in particular the three dimensional structure of CYP2A6 complexed with coumarin, methoxsalen, (5-(pyridin-3-yl)furan-2-yl)methanamine or 4,4'-dipyridyldisulfide, using information obtained from analysis of a cytochrome P450 2A-ligand complex crystal. An aspect of the present teachings comprises using the three dimensional structure of a crystalline cytochrome P450 2-ligand complex to derive the three dimensional structure of another Cytochrome-Ligand Complex. Therefore, the crystalline CYP2A6 complexed with coumarin, methoxsalen, (5-(pyridin-3-yl)furan-2-yl)methanamine or 4,4'-dipyridyldisulfide and the three dimensional structure of CYP2A6 complexed with coumarin, methoxsalen, (5-(pyridin-3-yl)furan-2-yl)methanamine or 4,4'-dipyridyldisulfide permits one of ordinary skill in the art to now derive the three dimensional structure, and models thereof, of any cytochrome P450-ligand complex. The derivation of the structure of any Cytochrome-Ligand Complex can now be achieved even in the absence of having crystal structure data for such other Cytochrome-Ligand Complexes, and when the crystal structure of another Cytochrome-Ligand Complex is available, the modeling of the three dimensional structure of the new Cytochrome-Ligand Complex can be refined using the knowledge already gained from the Cytochrome-Ligand Complex structure.

In some configurations of the present teachings, the absence of crystal structure data for other Cytochrome-Ligand Complexes, the three dimensional structures of other Cytochrome-Ligand Complex can be modeled, taking into account differences in the amino acid sequence of the other Cytochrome-Ligand Complex. Moreover, the present teachings allow for structure-based drug design of compounds which affect the activity of virtually any cytochrome P450, particularly a CYP2 family member, more particularly a CYP2A subfamily member, and more particularly a CYP2A6 such as a human CYP2A6.

One aspect of the present teachings includes a three dimensional structure of a Cytochrome-Ligand Complex, in which the atomic coordinates of the Cytochrome-Ligand Complex are generated by a method comprising: (a) providing a Cytochrome P450 complexed with a ligand in crystalline form; (b) generating an electron-density map of the crystalline Cytochrome P450 complexed with the ligand; and (c) analyzing the electron-density map to produce the atomic coordinates. For example, the structure of human CYP2A6 complexed with coumarin, methoxsalen, (5-(pyridin-3-yl)furan-2-yl)methanamine or 4,4'-dipyridyldisulfide are provided herein.

In some aspects, crystals of CYP2A6 in complex with coumarin can be prepared by mixing a protein solution comprising CYP 2A6, coumarin, and a non-ionic detergent with a crystallization solution comprising a polyethylene glycol polymer, a buffer, and ammonium sulfate. A high resolution data set can be collected from these crystals. Similarly, crystals of a CYP2A6-methoxsalen complex can be prepared by mixing a protein solution comprising CYP2A6, methoxsalen, and a non-ionic detergent with a crystallization solution comprising a polyethylene glycol polymer, a buffer, and ammonium sulfate. (5-(pyridin-3-yl)furan-2-yl)methanamine and 4,4'-dipyridyldisulfide crystals can be prepared similarly. Crystals prepared by these methods can be used to generate initial datasets.

In various aspects of the present teachings, X-ray diffraction data for a CYP2A6 in complex with a coumarin, methoxsalen, (5-(pyridin-3-yl)furan-2-yl)methanamine or 4,4'-dipyridyldisulfide can be collected on an individual crystal using methods well known to skilled artisans. In some configurations, initial data for the coumarin complex can be phased in the $P2_1$ space group by molecular replacement in AMoRe using a model of CYP2C8 (PDB Accession No. 1 PQ2) in which non-equivalent side-chains are replaced with alanine residues. In some configurations, initial data for other complexes can be phased in the $P2_1$ space group by isomorphous replacement using a model of CYP2A6 (Table 2, Protein DataBank Accession No. 1Z10). For data refinement, four-fold NCS restraints can be applied to each of the monomers in the asymmetric unit. During later stages of refinement, NCS restraints can be released to allow for differences in each of the monomers. For example, the model for the initial coumarin complex can be further refined against data to about 2.65 Å using multiple rounds of torsion angle simulated annealing. In a final stage, isotropic individual B-factor refinement can be used. In some aspects of the invention, a model generated in this manner can be used to phase the data set for the high resolution coumarin complex, which can be further built and used to phase a methoxsalen data set. In various aspects, models for the coumarin and methoxsalen complexes can be refined against data such as 2.05 Å and 1.90 Å data using multiple rounds of conjugant gradient least-squares minimization, torsion angle simulated annealing and isotropic individual B-factor refinement using a computer program such as CNS (Brunger, A. T. et al. Crystallography & NMR system: A new software suite for macromolecular structure determination. Acta Crystallogr. D. Biol. Crystallogr. 1998, 54 (Pt 5), 905-921). During the final stages of refinement of the coumarin and methoxsalen complexes, ligands, substrates and water molecules can be added. Multiple cycles of editing and adjustment of the model into $\sigma_A$-weighted $2|F_o|-|f_c|$, $1|F_o|-|f_c|$ and $2|F_o|-|f_c|$ composite omit maps can be performed using the graphics program O (Jones, T. A. and Kjeldgaard, M. Electron-Density Map Interpretation. Methods Enzymol. 1997, 277, 173-208). In some configurations, molecular graphics can be generated using a computer program such as PyMOL (available from DeLano Scientific, LLC (South San Francisco, Calif.; pymol.sourceforge.net). Probe accessible cavity volumes can be calculated with the aid of a computer program such as VOIDOO (Tan, Y. Z. et al. Competitive interactions between CYP2A6 and cytochrome P450 2E1 for NADPH-cytochrome P450 oxidoreductase in the microsomal membranes produced by a baculovirus expression system. Arch. Biochem. Biophys. 342, 82-91 (1997)). In these calculations, a probe radius such as 1.4 Å and grid spacing such as 0.33 Å can be used.

According to the present teachings, a three dimensional structure of the CYP2A6 protein complexed with 1,2-benzopyrone, 8-methoxypsoralen, (5-(pyridin-3-yl) furan-2-yl) methanamine or 4,4'-dipyridyldisulfide can be used to derive a model of the three dimensional structure of another Cytochrome-Ligand Complex (i.e., a structure to be modeled). As used herein, a "structure" of a protein refers to the components and the manner of arrangement of the components to constitute the protein. As used herein, the term "model" refers to a representation in a tangible medium of the three dimensional structure of a protein, polypeptide or peptide. For example, a model can be a representation of the three dimensional structure in an electronic file, on a computer screen, on a piece of paper (i.e., on a two dimensional medium), and/or as a ball-and-stick figure. Physical three-dimensional models are tangible and include, but are not limited to, stick models and space-filling models. The phrase "imaging the model on a computer screen" refers to the ability to express (or represent) and manipulate the model on a computer screen using appropriate computer hardware and software technology known to those skilled in the art. Such technology is available from a variety of sources including, for example, ACCELERYS® (San Diego, Calif.). The phrase "providing a picture of the model" refers to the ability to generate a "hard copy" of the model. Hard copies include both motion and still pictures. Computer screen images and pictures of the model can be visualized in a number of formats including space-filling representations, α-carbon traces, ribbon diagrams and electron density maps.

Suitable target Cytochrome-Ligand Complex structures to model using a method of the present teachings include any cytochrome P450 protein, polypeptide or peptide, including monomers and multimers of a cytochrome P450 protein that is substantially structurally related to a CYP2A6 protein complexed with coumarin or methoxsalen, e.g., 1,2-benzopyrone, 8-methoxypsoralen, (5-(pyridin-3-yl)furan-2-yl)methanamine or 4,4'-dipyridyldisulfide. In various aspects, a target Cytochrome-Ligand Complex structure that is substantially structurally related to a different Cytochrome-Ligand Complex can include a target Cytochrome-Ligand Complex structure having an amino acid sequence that is at least about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence of a eukaryotic CYP2A6 protein such as a human CYP2A6 protein, in particular an amino acid sequence comprising, consisting essentially of, or consisting of a sequence set forth herein as SEQ ID NO: 2 or SEQ ID NO: 3. In these configurations, a sequence alignment program such as BLAST (supra) can be used to aid in the analysis. In various aspects of the present teachings, target Cytochrome-Ligand Complex structures to model include proteins comprising amino acid sequences that are at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to amino acid sequence SEQ ID NO: 2 or SEQ ID NO: 3 when comparing suitable regions of the sequence, such as the amino acid sequence for a ligand or substrate binding site of any one of the amino acid sequences, when using an alignment program such as BLAST (supra) to align the amino acid sequences.

In various configurations of the present teachings, a structure can be modeled using techniques generally described by, for example, Sali, Current Opinions in Biotechnology, vol. 6, pp. 437-451, 1995, and algorithms can be implemented in program packages such as Insight II, available from ACCELERYS® (San Diego, Calif.). Use of INSIGHT II® HOMOLOGY requires an alignment of an amino acid sequence of a known structure having a known three dimensional structure with an amino acid sequence of a target structure to be modeled. The alignment can be a pairwise alignment or a multiple sequence alignment including other related sequences (for example, using the method generally described by Rost, Meth. Enzymol., vol. 266, pp. 525-539, 1996) to improve accuracy. Structurally conserved regions can be identified by comparing related structural features, or by examining the degree of sequence identity between the known structure and the target structure. Certain coordinates for the target structure are assigned using known structures from the known structure. Coordinates for other regions of the target structure can be generated from fragments obtained from known structures such as those found in a resource such as the Protein Data Bank. Conformation of side chains of the target structure can be assigned with reference to what is sterically allowable and using a library of rotamers and their frequency of occurrence (as generally described in Ponder and Richards, J. Mol. Biol., vol. 193, pp. 775-791, 1987). The resulting model of the target structure, can be refined by molecular mechanics to ensure that the model is chemically and conformationally reasonable.

Accordingly, one aspect of the present teachings is a method to derive a model of the three dimensional structure of a target cytochrome P450 2A-ligand complex structure, the method comprising the steps of: (a) providing an amino acid sequence of a Cytochrome-Ligand Complex and an amino acid sequence of a target ligand-complexed cytochrome P450; (b) identifying structurally conserved regions shared between the Cytochrome-Ligand Complex amino acid sequence and the target ligand-complexed cytochrome P450 amino acid sequence; (c) determining atomic coordinates for the target ligand-complexed cytochrome P450 by assigning said structurally conserved regions of the target ligand-complexed cytochrome P450 to a three dimensional structure using a three dimensional structure of a Cytochrome-Ligand Complex based on atomic coordinates that substantially conform to the atomic coordinates represented in Table 1 or Table 2, to derive a model of the three dimensional structure of the target ligand-complexed cytochrome P450 amino acid sequence. In one aspect, a model of the present teachings comprises a computer model. Generation of a computer model can, in some configurations, comprise electronically simulating structural assignments to derive a computer model of a three dimensional structure of a target ligand-complexed cytochrome P450 2A amino acid sequence.

Another aspect of the present teachings is a method to derive a computer model of the three dimensional structure of a target ligand-complexed cytochrome P450 2A structure for which a crystal has been produced (referred to herein as a "crystallized target structure"). A suitable method to produce such a model includes the method comprising molecular replacement. Methods of molecular replacement are generally known by those of skill in the art and are performed in a software program including, for example, X-PLOR available from ACCELERYS® (San Diego, Calif.). In various aspects, a crystallized target ligand-complexed cytochrome P450 structure useful in a method of molecular replacement according to the present teachings has an amino acid sequence that is at least about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the amino acid sequence of the search structure (e.g., CYP2A6), when the two amino acid sequences are compared using an alignment program such as BLAST (supra). A suitable search structure of the present teachings includes an Cytochrome-Ligand Complex having a three dimensional structure that substantially conforms with the atomic coordinates listed in Table 1, Table 2, Table 4 or Table 5.

Another aspect of the present teachings is a method for determining a three dimensional structure of a target Cytochrome-Ligand Complex. Such a method is useful for identifying structures that are related to the three dimensional structure of a Cytochrome-Ligand Complex based only on the three dimensional structure of the target structure. For example, the present method enables identification of structures that do not have high amino acid sequence identity with a CYP2A6 protein but share three dimensional structure similarities of a ligand-complexed CYP2A6. In various aspects of the present teachings, a method to determine a three dimensional structure of a target Cytochrome-Ligand Complex structure can comprise: (a) providing an amino acid sequence of a target structure, wherein the three dimensional structure of the target structure is not known; (b) analyzing the pattern of folding of the amino acid sequence in a three dimensional conformation by fold recognition; and (c) comparing the pattern of folding of the target structure amino acid sequence with the three dimensional structure of a Cytochrome-Ligand Complex to determine the three dimensional structure of the target structure, wherein the three dimensional structure of the Cytochrome-Ligand Complex substantially conforms to the atomic coordinates represented in Table 1, Table 2, Table 4 and/or Table 5. For example, methods of fold recognition can include the methods generally described in Jones, Curr. Opinion Struc. Biol., vol. 7, pp. 377-387, 1997. Such folding can be analyzed based on hydrophobic and/or hydrophilic properties of a target structure.

One aspect of the present teachings includes a three dimensional computer image of the three dimensional structure of a Cytochrome-Ligand Complex. In one aspect, a computer image is created to a structure which substantially conforms with the three dimensional coordinates listed in Table 1, Table 2, Table 4 and/or Table 5. A computer image of the present teachings can be produced using any suitable software program, including, but not limited to, PyMOL (supra). Suitable computer hardware useful for producing an image of the present teachings are known to those of skill in the art.

Another aspect of the present teachings relates to a computer-readable medium encoded with a set of three dimensional coordinates represented in Table 1, Table 2, Table 4 and/or Table 5, wherein, using a graphical display software program, the three dimensional coordinates create an electronic file that can be visualized on a computer capable of representing said electronic file as a three dimensional image. Yet another aspect of the present teachings relates to a computer-readable medium encoded with a set of three dimensional coordinates of a three dimensional structure which substantially conforms to the three dimensional coordinates represented in Table 1, Table 2, Table 4 and/or Table 5 wherein, using a graphical display software program, the set of three dimensional coordinates create an electronic file that can be visualized on a computer capable of representing said electronic file as a three dimensional image.

The present teachings also include a three dimensional model of the three dimensional structure of a target structure, such a three dimensional model being produced by the method comprising: (a) providing an amino acid sequences of an cytochrome P450 comprised by a Cytochrome-Ligand Complex and an amino acid sequence of a target Cytochrome-Ligand Complex structure; (b) identifying structurally conserved regions shared between the cytochrome P450 amino acid sequence and the amino acid sequence comprised by the target Cytochrome-Ligand Complex structure; (c) determining atomic coordinates for the target Cytochrome-Ligand Complex by assigning the structurally conserved regions of the target Cytochrome-Ligand Complex to a three dimensional structure using a three dimensional structure of the cytochrome P450 comprised by a Cytochrome-Ligand Complex based on atomic coordinates that substantially conform to the atomic coordinates represented in Table 1, Table 2, Table 4 and/or Table 5 to derive a model of the three dimensional structure of the target Cytochrome-Ligand Complex. In one aspect, the model comprises a computer model.

Any isolated cytochrome P450 protein can be used with the methods of the present teachings. An isolated cytochrome P450 protein can be isolated from its natural milieu or produced using recombinant DNA technology (e.g., polymerase chain reaction (PCR) amplification, cloning) or chemical synthesis. To produce recombinant cytochrome P450 protein, a nucleic acid molecule encoding cytochrome P450 protein can be inserted into any vector capable of delivering the nucleic acid molecule into a host cell. A nucleic acid molecule of the present teachings can encode any portion of a cytochrome P450 protein, in various aspects a full-length cytochrome P450 protein, and in various aspects a soluble form of cytochrome P450 protein (i.e., a form of cytochrome P450 protein capable of being secreted by a cell that produces such protein). A suitable nucleic acid molecule to include in a recombinant vector, and particularly in a recombinant molecule, includes a nucleic acid molecule encoding a protein having the amino acid sequence represented by SEQ ID NO: 2 or SEQ ID NO: 3.

A recombinant vector can be either RNA or DNA, either prokaryotic or eukaryotic, and typically is a virus or a plasmid. In various aspects, a nucleic acid molecule encoding an cytochrome P450 protein is inserted into a vector comprising an expression vector to form a recombinant molecule. As used herein, an expression vector is a DNA or RNA vector that is capable of transforming a host cell and of affecting expression of a specified nucleic acid molecule. Expression vectors of the present teachings include any vectors that function (i.e., direct gene expression) in recombinant cells of the present teachings, including in bacterial, fungal, endoparasite, insect, other animal, and plant cells.

An expression vector can be transformed into any suitable host cell to form a recombinant cell. A suitable host cell includes any cell capable of expressing a nucleic acid molecule inserted into the expression vector. For example, a prokaryotic expression vector can be transformed into a bacterial host cell. One method to isolate cytochrome P450 protein useful for producing ligand-complexed cytochrome P450 crystals includes recovery of recombinant proteins from cell cultures of recombinant cells expressing such cytochrome P450 protein.

Cytochrome P450 proteins of the present teachings can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, chromatofocusing and differential solubilization. In various aspects of the present teachings, an cytochrome P450 protein is purified in such a manner that the protein is purified sufficiently for formation of crystals useful for obtaining information related to the three dimensional structure of an Cytochrome-Ligand Complex. In some aspects, a composition of cytochrome P450 protein is about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% pure.

Another aspect of the present teachings includes a composition comprising a Cytochrome-Ligand Complex in a crystalline form (i.e., Cytochrome-Ligand Complex crystals). As used herein, the terms "crystalline Cytochrome-Ligand Complex" and "Cytochrome-Ligand Complex crystal" both refer to crystallized a Cytochrome-Ligand Complex and are intended to be used interchangeably. In various aspects of the present teachings, a crystalline Cytochrome-Ligand Complex is produced using the crystal formation method described in the Examples.

In particular, the present teachings include a composition comprising CYP2A6 complexed with coumarin, methoxsalen, (5-(pyridin-3-yl)furan-2-yl)methanamine or 4,4'-dipyridyldisulfide in a crystalline form (i.e., ligand-complexed CYP2A6 crystals). As used herein, the terms "crystalline ligand-complexed CYP2A6" and "ligand-complexed CYP2A6 crystal" both refer to crystallized CYP2A6 complexed with coumarin, methoxsalen, (5-(pyridin-3-yl)furan-2-yl)methanamine or 4,4'-dipyridyldisulfide. These terms are intended to be used interchangeably. In various aspects of the present teachings, a crystal ligand-complexed CYP2A6 is produced using the crystal formation method described in the Examples. In some aspects, a composition of the present teachings includes ligand-complexed CYP2A6 molecules arranged in a crystalline manner in a space group $P2_1$, so as to form a unit cell of dimensions a=70.62 Å, b=157.59 Å, c=103.54 Å, and $\beta$=92.25° (CYP2A6-coumarin) or a=70.66 Å, b=159.03 Å, c=103.88 Å, and $\beta$=92.00° (CYP2A6-methoxsalen).

A suitable crystal of the present teachings provides X-ray diffraction data for determination of atomic coordinates of the ligand-complexed CYP2A6 to a resolution of about 4.2 Å, and in some aspects about 3.0 Å, and in other aspects to about 1.5 Å.

According to an aspect of the present teachings, a crystalline Cytochrome-Ligand Complex can be used to determine the ability of a compound of the present teachings to bind to a cytochrome P450 in a manner predicted by a structure based drug design method of the present teachings. In various aspects of the present teachings, a Cytochrome-Ligand Complex crystal is soaked in a solution containing a chemical compound of the present teachings. Binding of the chemical compound to the crystal is then determined by methods standard in the art such as those provided in the Examples section herein.

One aspect of the present teachings is a therapeutic composition. A therapeutic composition of the present teachings comprises one or more therapeutic compounds. In one aspect, a therapeutic composition involving a cytochrome P450 is provided which promotes smoking cessation. For example, a therapeutic composition of the present teachings can inhibit (i.e., prevent, block) binding of a cytochrome P450 on a cell having a cytochrome P450 (e.g., eukaryotic cells) to a, e.g., a cytochrome P450 ligand or substrate by interfering with a binding site of a cytochrome P450. As used herein, the term "binding site" refers to the region of a molecule to which another molecule specifically binds. In one aspect of the present teachings, a method is provided for inducing smoking cessation in a subject comprising administering to the subject in need thereof a therapeutically effective amount of a therapeutic composition of the present teachings.

Suitable inhibitory compounds of the present teachings are compounds that interact directly with an cytochrome P450 protein, and in various aspects a CYP2A6 protein, thereby inhibiting the binding of a cytochrome P450 ligand or substrate, e.g., coumarin, methoxsalen, (5-(pyridin-3-yl)furan-2-yl)methanamine or 4,4'-dipyridyldisulfide, to a cytochrome P450 by blocking a binding site of a cytochrome P450 (referred to herein as substrate analogs). A cytochrome P450 substrate analog refers to a compound that interacts with (e.g., binds to, associates with, modifies) a binding site of a cytochrome P450. A cytochrome P450 substrate analog can, for example, comprise a chemical compound that mimics 1,2-benzopyrone, 8-methoxypsoralen, (5-(pyridin-3-yl)furan-2-yl)methanamine, 4,4'-dipyridyldisulfide, or another ligand or substrate of a binding site of a cytochrome P450.

According to the present teachings, suitable therapeutic compounds of the present teachings include peptides or other organic molecules, and inorganic molecules. Suitable organic molecules include small organic molecules. In various aspects, a therapeutic compound of the present teachings is not harmful (e.g., toxic) to an animal when such compound is administered to an animal. Peptides refer to a class of compounds that is less than about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 kDa and yields two or more amino acids upon hydrolysis. A polypeptide is comprised of two or more peptides. As used herein, a protein is comprised of one or more polypeptides. Suitable therapeutic compounds to design include peptides composed of "L" and/or "D" amino acids that are configured as normal or retroinverso peptides, peptidomimetic compounds, small organic molecules, or homo- or hetero-polymers thereof, in linear or branched configurations.

Therapeutic compounds of the present teachings can be designed using structure-based drug design. Structure-based drug design refers to the use of computer simulation to predict a conformation of a peptide, polypeptide, protein, or conformational interaction between a peptide or polypeptide, and a therapeutic compound. In the present teachings, knowledge of the three dimensional structure of the coumarin, methoxsalen, (5-(pyridin-3-yl)furan-2-yl)methanamine and 4,4'-dipyridyldisulfide binding sites of a cytochrome P450 provide one of skill in the art the ability to design a therapeutic compound that 1) specifically binds to cytochrome P450s, or to a selected subset of cytochrome P450s, 2) is stable, and 3) results in inhibition of a biological response such as procarcinogen activation in a cell having a cytochrome P450. For example, knowledge of the three dimensional structure of the coumarin, methoxsalen, (5-(pyridin-3-yl)furan-2-yl)methanamine and 4,4'-dipyridyldisulfide binding sites of a cytochrome P450 provides to a skilled artisan the ability to design an analog of coumarin, methoxsalen, (5-(pyridin-3-yl)furan-2-yl)methanamine or 4,4'-dipyridyldisulfide which can function as a substrate or ligand of cytochrome P450s or with high specificity to a selected subset of cytochrome P450s, e.g., CYP2A6, and in particular human CYP2A6.

Suitable structures and models useful for structure-based drug design are disclosed herein. Models of target structures to use in a method of structure-based drug design include models produced by any modeling method disclosed herein, such as, for example, molecular replacement and fold recognition related methods. In some aspects of the present teachings, structure based drug design can be applied to a structure of CYP2A6 in complex with coumarin, methoxsalen, (5-(pyridin-3-yl)furan-2-yl)methanamine and 4,4'-dipyridyldisulfide, and to a model of a target cytochrome P450 structure.

One aspect of the present teachings is a method for designing a drug which interferes with an activity of a cytochrome P450. In various configurations, the method comprises providing a three-dimensional structure of a Cytochrome-Ligand Complex comprising the cytochrome P450 and at least one ligand of the cytochrome; and designing a chemical compound which is predicted to bind to the cytochrome P450. The designing can comprise using physical models, such as, for example, ball-and-stick representations of atoms and bonds, or on a digital computer equipped with molecular modeling software. In some configurations, these methods can further include synthesizing the chemical compound, and evaluating the chemical compound for ability to interfere with an activity of the cytochrome P450.

Suitable three dimensional structures of a Cytochrome-Ligand Complex and models to use with the present method are disclosed herein. According to the present teachings, designing a compound can include creating a new chemical compound or searching databases of libraries of known compounds (e.g., a compound listed in a computational screening database containing three dimensional structures of known compounds). Designing can also include simulating chemical compounds having substitute moieties at certain structural features. In some configurations, designing can include selecting a chemical compound based on a known function of the compound. In some configurations designing can comprise computational screening of one or more databases of compounds in which three dimensional structures of the compounds are known. In these configurations, a candidate compound can be interacted virtually (e.g., docked, aligned, matched, interfaced) with the three dimensional structure of a Cytochrome-Ligand Complex by computer equipped with software such as, for example, the AutoDock software package, (The Scripps Research Institute, La Jolla, Calif.) or described by Humblet and Dunbar, Animal Reports in Medicinal Chemistry, vol. 28, pp. 275-283, 1993, M Venuti, ed., Academic Press. Methods for synthesizing candidate chemical compounds are known to those of skill in the art.

Various other methods of structure-based drug design are disclosed in references such as Maulik et al., 1997, Molecular Biotechnology: Therapeutic Applications and Strategies, Wiley-Liss, Inc., which is incorporated herein by reference in its entirety. Maulik et al. disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional structures and small fragment probes, followed by linking together of favorable probe sites.

In one aspect, a chemical compound of the present teachings that binds to an Cytochrome-Ligand Complex can be a chemical compound having chemical and/or stereochemical complementarity with a CYP2A6, e.g., a CYP2A6 ligand, such as, for example, 1,2-benzopyrone, 8-methoxypsoralen, (5-(pyridin-3-yl)furan-2-yl)methanamine or 4,4'-dipyridyldisulfide. In some configurations, a chemical compound that binds to a cytochrome P450 can associate with an affinity of at least about $10^{-6}$ M, at least about $10^{-7}$ M, or at least about $10^{-8}$ M.

Several sites of cytochrome P450s can be targets for structure based drug design. These sites include, in non-limiting example residues which contact a ligand or substrate such as 8-methoxysalen or 1,2-benzopyrone (e.g., Phe107, Phe111, Phe118, Phe209, Phe480, Va1117, Asn297, Ile 300, Gly301, Thr305, Ile366, Leu370). Such sites may include several amino acids toward either the N- or C-terminus in addition to the specific listed amino acids.

Drug design strategies as specifically described above with regard to residues and regions of the ligand-complexed CYP2A6 crystal can be similarly applied to the other cytochrome P450 structures, including other cytochrome P450 2 and cytochrome P450 2A structures disclosed herein. One of ordinary skill in the art, using the art recognized modeling programs and drug design methods, many of which are described herein, can modify the cytochrome P450 design strategy according to differences in amino acid sequence. For example, this strategy can be used to design compounds which regulate smoking cessation or procarcinogen activation in other cytochrome P450s. In addition, one of skill in the art can use lead compound structures derived from one cytochrome P450, such as CYP2A6, and take into account differences in amino acid residues in other cytochrome P450s, such as, for example, CYP2C8.

In the present method of structure-based drug design, it is not necessary to align a candidate chemical compound (I.e., a chemical compound being analyzed in, for example, a computational screening method of the present teachings) to each residue in a target site. Suitable candidate chemical compounds can align to a subset of residues described for a target site. In some configurations of the present teachings, a candidate chemical compound can comprise a conformation that promotes the formation of covalent or noncovalent cross-linking between the target site and the candidate chemical compound. In certain aspects, a candidate chemical compound can bind to a surface adjacent to a target site to provide an additional site of interaction in a complex. For example, when designing an antagonist (i.e., a chemical compound that inhibits the binding of a ligand to a cytochrome P450 by blocking a binding site or interface), the antagonist can be designed to bind with sufficient affinity to the binding site or to substantially prohibit a ligand (i.e., a molecule that specifically binds to the target site) from binding to a target area. It will be appreciated by one of skill in the art that it is not necessary that the complementarity between a candidate chemical compound and a target site extend over all residues specified here.

In various aspects, the design of a chemical compound possessing stereochemical complementarity can be accomplished by means of techniques that optimize, chemically or geometrically, the "fit" between a chemical compound and a target site. Such techniques are disclosed by, for example, Sheridan and Venkataraghavan, Acc. Chem. Res., vol. 20, p. 322, 1987: Goodford, J. Med. Chem., vol. 27, p. 557, 1984; Beddell, Chem. Soc. Reviews, vol. 279, 1985; Hol, Angew. Chem., vol. 25, p. 767, 1986; and Verlinde and Hol, Structure, vol. 2, p. 577, 1994, each of which are incorporated by this reference herein in their entirety.

Some aspects of the present teachings for structure-based drug design comprise methods of identifying a chemical compound that complements the shape of a cytochrome P450 or a structure that is related to a cytochrome P450. Such method is referred to herein as a "geometric approach". In a geometric approach of the present teachings, the number of internal degrees of freedom (and the corresponding local minima in the molecular conformation space) can be reduced by considering only the geometric (hard-sphere) interactions of two rigid bodies, where one body (the active site) contains "pockets" or "grooves" that form binding sites for the second body (the complementing molecule, such as a ligand).

The geometric approach is described by Kuntz et al., J. Mol. Biol., vol. 161, p. 269, 1982, which is incorporated by this reference herein in its entirety. The algorithm for chemical compound design can be implemented using a software program such as AutoDock, available from the The Scripps Research Institute (La Jolla, Calif.). One or more extant databases of crystallographic data (e.g., the Cambridge Structural Database System maintained by University Chemical Laboratory, Cambridge University, Lensfield Road, Cambridge CB2 IEW, U.K. or the Protein Data Bank maintained by Rutgers University) can then be searched for chemical compounds that approximate the shape thus defined. Chemical compounds identified by the geometric approach can be modified to satisfy criteria associated with chemical complementarity, such as hydrogen bonding, ionic interactions or Van der Waals interactions.

In some aspects, a therapeutic composition of the present teachings can comprise one or more therapeutic compounds. A therapeutic composition can further comprise other compounds capable of inducing smoking cessation or inhibiting procarcinogen activation. A therapeutic composition of the present teachings can be used to treat disease in an animal such as, for example, a human in need of treatment by administering such composition to an animal. Non-limiting examples of animals to treat include mammals, marsupials, reptiles and birds, humans, companion animals, food animals, zoo animals and other economically relevant animals (e.g., race horses and animals valued for their coats, such as chinchillas and minks). Additional animals to treat include dogs, cats, horses, cattle, sheep, swine, chickens, turkeys. Accordingly, in some aspects, animals to treat include humans, dogs and cats.

A therapeutic composition of the present teachings can also include an excipient, an adjuvant and/or carrier. Suitable excipients include compounds that the animal to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one aspect of the present teachings, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

Acceptable protocols to administer therapeutic compositions of the present teachings in an effective manner include individual dose size, number of doses, frequency of dose administration, and mode of administration. Determination of such protocols can be accomplished by those skilled in the art. Modes of administration can include, but are not limited to, inhalation, subcutaneous, intradermal, intravenous, intranasal, oral, transdermal, intraocular and intramuscular routes.

TABLE 6

Data collection and refinement statistics for CYP2A6dH

| Cytochrome P450 Construct | 2A6dH | 2A6dH |
|---|---|---|
| Complex | methoxsalen | coumarin |
| P2$_1$ Unit Cell (a,b,c,β) | 70.66, 159.03, 103.88, 92.00° | 70.62, 157.59, 103.54, 92.25° |
| Data Collection | | |
| Beam line | SSRL BL9-2 | SSRL BL 11-1 |
| Wavelength (Å) | 1.03 and 0.98 | 0.98 |
| Resolution Range (Å) | 50-2.05 | 50-1.9 |
| Unique Reflections > 0.0σ\|F\| | 134,956 | 164,494 |
| Redundancy [1] | 2.2 (2.4) | 3.4 (3.2) |
| Completeness (%) [1] | 94.3 (90.5) | 98.6 (96.6) |
| <i/σI> [1] | 30.0 (2.6) | 22.4 (2.1) |
| Rsymm(I) [1] | 0.054 (0.243) | 0.108 (0.464) |
| Refinement | | |
| Rwork | 0.219 | 0.194 |
| Rfree | 0.261 | 0.230 |
| RMS deviation bonds (Å) | 0.011 | 0.019 |
| RMS deviation angles (deg) [2] | 1.44 | 1.79 |
| Model Residues/No. of atoms/Ave. B-factor (Å$^2$) | | |
| Protein [3] | 15039 53.9 | 15037 42.2 |
| Heme | 172 39.5 | 172 31.6 |
| Substrate | 64 84.6 | 44 60.4 |
| Water Molecules | 504 52.0 | 816 46.2 |

[1] Values for the highest resolution shell in parentheses. Values for Rsym are averaged between two resolution passes. Value for redundancy is averaged.
[2] Ramachandran plot for methoxsalen complex: 89.2% of the residues in the most favored regions, 10.2% in allowed regions, 0.3% in generously allowed regions, 0.2% in disfavored regions. Ramachandran plot for the coumarin complex: 90.5% of the residues in the most favored regions, 9.1% in allowed regions, 0.2% in generously allowed regions, 0.2% in disfavored regions.
[3] Residues 30 to 496, 32 to 495, 31 to 494, 31 to 494 molecules A-D respectively for the methoxsalen complex. Residues 30 to 494, 32 to 496, 31 to 494, 31 to 494 molecules A-D respectively for the courmarin complex. Residue L370 found in alternate conformations in coumarin complex.

TABLE 7

Data Collection and Refinement Statistics.

| Ligand | Aldrithiol ™ | (5-(pyridin-3-yl) furan-2-yl) methanamine |
|---|---|---|
| PDB Identifier | 2FDY | 2FDW |
| Resolution Range (Å) | 50.0-1.95 | 50.0-2.05 |
| Unique Reflections | 160,717 | 131,309 |
| Average Redundancy$_a$ | 3.4 (2.6) | 3.6 (3.6) |
| Completeness (%)$_a$ | 98.7 (91.3) | 93.9 (99.9) |
| (I/σaverage I)$_a$ | 7.6 (2.0) | 16.4 (2.1) |
| Rsymm (I)$_a$ | 0.089 (0.451) | 0.09 (0.669) |
| R (R$_{free}$)$_a$ | 0.212 (0.250) | 0.205 (0.22) |
| RMSD bonds (Å) | 0.006 | 0.006 |
| RMSD angles (°) | 1.26 | 1.23 |

$_a$Values are for the highest resolution shell. All data presented in the table was collected at the Stanford Synchrotron Radiation Laboratory on beamline 9-1.

EXAMPLES

The methods and compositions described herein utilize laboratory techniques which are well known to skilled artisans and which can be found in laboratory manuals such as Sambrook, J., Fritsch, E. F. and Maniatis, T. (1989) Molecular Cloning: A Laboratory Manual, 2nd ed. Cold Spring Harbor Laboratory Press, Cold Spring Harbor, N.Y.

Example 1

This Example Illustrates CYP2A6DH Construct Generation

The CYP2A6dH construct was designed to produce a conditionally soluble enzyme that retains wild-type activity. To accomplish this goal, DNA encoding the N-terminal transmembrane signal anchor region composed of the first 28 residues was replaced with DNA encoding the sequence MAKKTS (SEQ ID NO: 4), which had been optimized for the expression and crystallization of rabbit P450 2C5 (Johnson, E. F. The 2002 Bernard B. Brodie Award lecture: deciphering substrate recognition by drug-metabolizing cytochromes P450. Drug Metab Dispos. 31, 1532-1540 (2003). In addition to the N-terminal mutations, DNA encoding a four residue histidine tag was added to the C-terminus to aid in purification. This construct is referred to as the CYP2A6dH construct. This strategy produced a truncated protein which crystallized in the P2$_1$ space group and demonstrated a K$_m$ of 0.23±0.03 μM and V$_{max}$ of 10.83±1.38 nmols/min/nmol P450 for coumarin 7-hydroxylation when reconstituted with P450 reductase. Dissociation constants for the binding of purified CYP2A6dH were determined for coumarin and 8-methoxypsoralen by monitoring substrate dependent conversion of the enzyme to a high spin ferric heme protein and are 0.27 μM and 1.85 μM, respectively. Similar values of coumarin hydroxylation (mean values of Km are 0.40 μM and V$_{max}$ are 6.34 nmols/min/nmol P450) and methoxsalen inhibition (K$_i$=1.9 μM) were reported by Koenigs et al. (Mechanism-based inactivation of human liver cytochrome CYP2A6 by 8-methoxypsoralen. Drug Metab. Dispos. 25, 1407-1415 (1997)) for full length wild-type CYP2A6 in microsomal preparations from a panel of 12 human liver microsomes. These results suggest that the modification to the N- and C-termini did not significantly alter the substrate binding or catalytic activity of the enzyme.

In this example, a vector was designed for expression of a cytochrome CYP2A6 comprising a truncated the N-terminal transmembrane signal anchor domain while expressing residues 29-494 of the catalytic domain without internal modifications that may alter catalytic activity. SEQ ID NO: 2. In this example, DNA encoding residues 1-28 was replaced with DNA encoding the amino acid sequence MAKKTS using a polymerase chain reaction. Additionally, DNA encoding a four residue histidine tag was added to the C-terminus. This DNA construct was expressed in *Escherichia coli* and is referred to as CYP2A6dH. CYP2A6dH was expressed and purified as previously described for P450 2C5 with minor modifications (Johnson, E. F. The 2002 Bernard B. Brodie Award lecture: deciphering substrate recognition by drug-metabolizing cytochromes P450. Drug Metab Dispos. 31, 1532-1540 (2003). The sequence of the polypeptide encoded by this construct is disclosed herein as SEQ ID NO: 3.

Example 2

This example illustrates enzyme activity of the CYP2A6dH polypeptide.

In this example, to determine catalytic properties for the purified protein, CYP2A6dH was reconstituted with *E. coli*-expressed purified human reductase in the absence of L-α-dilauroyl-L-α-lecithin with slight modifications to the protocol described by Tan et al. (Competitive interactions between CYP2A6 and cytochrome P450 2E1 for NADPH-cytochrome P450 oxidoreductase in the microsomal membranes produced by a baculovirus expression system. Arch. Biochem. Biophys. 342, 82-91 (1997)). 10 pmol CYP2A6dH was incubated on ice for 10 min. with 0.06 U human reductase at a ratio of 1:6, CYP2A6dH to reductase in a final volume of 10 μl. 1.2 benzopyrone at concentrations ranging from 25 μM to 2.5 mM were then added in 10 μA aliquots, along with 430 μL of 50 mM Tris pH 7.4. The reaction mixture was allowed to equilibrate at 37° C. for 3 min. To start the reaction, 50 μl of an NADPH regeneration system (50 mM isocitrate, 50 mM MgCl$_2$, 5 U/ml isocitrate dehydrogenase and 10 mM NADPH) was added. The reaction was allowed to proceed for 5 min., and stopped by addition of 100 μl of cold 20% trichloroacetic acid. The components were centrifuged at 13,000 rpm. 10 μl of the supernatant was removed and added to 190 μl 100 mM Tris buffer, pH 9.0. the coumarin content was quantified fluorometrically (excitation at 368 nm and emission at 453 nm).

Example 3

This Example Illustrates Crystallization

In this example, the initial dataset was collected using a crystal prepared by mixing equal volumes of a protein solution containing 380 μM CYP2A6dH in XB, 1 mM coumarin, and 0.17% ANAPOE®-X-405 with crystallization well solution containing 30% Polyethylene glycol 4000, 100 mM Tris pH 8.5, 200 mM ammonium sulfate. The high resolution data set was collected from a crystal prepared by mixing equal volumes of a protein solution containing 540 μM CYP2A6dH in XB, 8.89 mM coumarin, and 0.2% ANAPOE®-X-405 with crystallization well solution containing 30% Polyethylene glycol 3350, 100 mM Tris pH 8.5, and 200 mM ammonium sulfate. Crystals of the methoxsalen complex were prepared by first diluting 540 μM CYP2A6dH 100 times in XB containing 100 μM methoxsalen and then concentrating the solution to the original volume. Equal volumes of protein solution containing ~540 μM CYP2A6dH methoxsalen complex in XB and 0.2% ANAPOE®-X-405 were combined with crystallization well solution containing 30% Polyethylene glycol3350, 100 mM Tris pH 8.5, and 200 mM ammonium sulfate, 100 μM Methoxsalen. All substrates and detergents were purchased from SIGMA (St. Louis, Mo.) and ANATRACE® (Maumee, Ohio), respectively. All crystals were grown by sitting drop vapor diffusion in 2.5 µl drops.

To reduce radiation damage induced by the X-ray beam, the crystals were frozen in liquid $N_2$. Crystals were flash cooled to 100 K in a stream of liquid $N_2$ using a cryoprotectant solution containing 700 µA of a 1:1 mixture of XB and crystallization well solution and 300 µA of 100% ethylene glycol.

Example 4

This Example Illustrates Collection of Diffraction Data

In this example, data for the coumarin and methoxsalen complex were collected on a single crystal cooled to 100 K at the Stanford Synchrotron Radiation Laboratory (SSRL, Palo Alto, Calif.) on beamline 11-1 for the coumarin complex and on beamline 9-2 for the methoxsalen complex. All data were processed in HKL2000®, and Scalepack was used to scale and reduce the data (Fukami, T. et al. A novel polymorphism of human CYP2A6 gene CYP2A6*17 has an amino acid substitution (V365M) that decreases enzymatic activity in vitro and in vivo. Clin. Pharmacol. Ther. 76, 519-527 (2004)). The initial data for the coumarin complex were phased in the $P2_1$ space group by molecular replacement in AMoRe using a model of CYP2C8 (PDB Accession No. 1 PQ2) in which non-equivalent side-chains were replace by alanine residues (Kitagawa, K., Kunugita, N., Kitagawa, M., & Kawamoto, T. CYP2A6*6, a novel polymorphism in cytochrome p450 2A6, has a single amino acid substitution (R128Q) that inactivates enzymatic activity. J. Biol. Chem. 276, 17830-17835 (2001)). The Mathews coefficient suggested that there were four molecules in the asymmetric unit, and four were found. During early stages of refinement, four-fold NCS restraints were applied to each of the monomers in the asymmetric unit. During later stages of refinement, NCS restraints were released to allow for differences in each of the monomers. The model for initial coumarin complex was refined against data to 2.65 Å using multiple rounds of torsion angle simulated annealing. In the final stage, one round of isotropic individual B-factor refinement was done. This model was used to phase the data set for the high resolution coumarin complex, which was further built and used to phase the methoxsalen data set. The models for the coumarin and methoxsalen complexes were refined against 2.05 Å and 1.90 Å data using multiple rounds of conjugant gradient least-squares minimization, torsion angle simulated annealing and isotropic individual B-factor refinement using the program CNS. During the final stages of refinement of the coumarin and methoxsalen complexes, substrates and water molecules were added. Data collection and structure refinement statistics for the coumarin and methoxsalen complexes can be found in Tables 1 and 2. Multiple cycles of editing and adjustment of the model into $\sigma_A$-weighted $2|F_o|-|f_c|$, $1|F_o|-|f_c|$ and $2|F_o|-|f_c|$ composite omit maps was performed using the graphics program O (Denton, T. T., Zhang, X., & Cashman, J. R. 5-Substituted, 6-Substituted, and Unsubstituted 3-Heteroaromatic Pyridine Analogues of Nicotine as Selective Inhibitors of Cytochrome P-450 2A6. J. Med. Chem. 48, 224-239 (2005)). Unless otherwise indicated, molecular graphics were generated in PyMOL (supra). All probe accessible cavity volumes were calculated with the program VOIDOO with a probe radius of 1.4 Å and grid spacing of 0.33 Å.

Example 5

This Example Illustrates Determination of Three Dimensional Structure

Data from a single crystal of a CYP2A6dH coumarin complex that diffracted to a limiting resolution of 2.65 Å was phased by molecular replacements using a model of cytochrome P450 2C8 (Protein Data Bank accession code 1 PQ2) in which non-equivalent side chains were replaced by alanine residues. As higher resolution data sets became available the current model was used to phase the new data set. Manual building of the peptide backbone and side-chains into electron density maps was continued. The final model was generated by subsequent fitting and refinement using data collected from a single crystal of the coumarin complex that diffracted to a limiting resolution of 1.9 Å. The resultant structure exhibited an R value of 0.194 and an $R_{free}$ value of 0.230 with four molecules in the asymmetric unit (Table 6). Residues 30-496, 32-495, 31-494, and 31-494 of chains A-D respectively, 816 water molecules, 4 molecules of coumarin and one glycerol molecule were defined by $2|Fo|-|Fc|$ $\sigma_A$ weighted electron density maps. Fitting and refinement of the methoxsalen complex utilized data collected for a single crystal of the complex that diffracted to a limiting resolution of 2.05 Å. The structure exhibits an R value of 0.219 and an $R_{free}$ value of 0.261 (Table 6). Residues 30-494, 32-495, 31-494, and 31-494 of chains A-D respectively, 4 molecules of methoxsalen, one molecule of glycerol and 521 water molecules were modeled into $2|Fo|-|Fc|$ $\sigma_A$-weighted electron density maps.

Example 6

This Example Illustrates Determination of Binding Constants by Visible Difference Spectroscopy In this example, the conversion of CYP2A6dH from a low spin to a high spin state in the presence of coumarin or methoxsalen was monitored by observing spectral changes from 260 nm to 700 nm at ambient temperature on a CARY 1 E UV-visible spectrophotometer. Purified CYP2A6dH was diluted to ~3 µM in 50 mM KPi pH 7.4, 500 mM NaCl, 20% glycerol, 1 mM EDTA (referred to as XB) in a 1-cm path length microcuvette. Freshly prepared aliquots of coumarin or methoxsalen dissolved in 50% methanol were added to the diluted protein, and the measurements were taken. The total concentration of methanol remained under 1%. Binding was monitored as the absorbance difference, ΔA, between the peak (~385 nm) and trough (~417 nm) of the difference spectrum. The apparent binding constant, Ks, and the extrapolated maximum spectral change, ΔAmax, were estimated from nonlinear least-squares regression fitting using the following equation:

$$\Delta A = \frac{\Delta A \max}{2P}\left[P+S+Ks - \sqrt{(P+S+Ks) \wedge 2 - 4PS}\,\right]$$

where S is the total concentration of ligand and P is the total concentration of P450.

Example 7

This Example Illustrates Substrate and Inhibitor Binding

In this example, the locations of the coumarin and methoxysalen molecules in the active site of CYP2A6 are defined by σA-weighted 2|Fo|-|Fc| omit electron density (FIGS. 4 and 5). The tertiary structures of the coumarin and methoxsalen complexes are very similar, with a RMSD of 0.27 Å for all equivalent Cα positions. Additionally, the RMSD for regions associated with the active site (101-120, 196-256, 288-318, 364-371 and 476-484) is 0.15 Å, demonstrating that there are essentially no structural changes in the backbone upon binding the larger methoxsalen molecule. Furthermore, differences in the positions of the side chains contacting the substrate molecules are also minimal (FIG. 8). In FIG. 8, two views (a) and (b) showing the superposed structures of the coumarin (arrow 120) and methoxsalen (arrow 121) complexes of CYP2A6 are provided. Oxygen atoms are indicated by arrow 113, nitrogen atoms are indicated by arrow 114, and carbon atoms are indicated by arrow 120 (coumarin complex) or arrow 121 (methoxsalen complex). Side chains within 5 Å of the ligands are displayed as a stick representation. The heme group is displayed as a stick figure. The pyran rings of each substrate are oriented so that the hydrogens interact with the π-electron system of Phe107. Moreover, the positions of the substrates and side-chains are highly similar in each of the molecules that constitute the asymmetric unit. However, Leu370 is found in two alternative positions in the A molecule of the coumarin complex indicating that it is not confined by substrate binding in the complex.

The electron density suggests that ketal oxygen of each molecule is oriented with the potential to form 3.3±0.13 and 2.9±0.02 Å hydrogen bonds with the side chain nitrogen of Asn297 for coumarin and methoxsalen, respectively (FIGS. 4 and 5). In FIG. 4, The active site cavity, located above the heme group, is rendered as a mesh and is indicated by arrow 108, the heme is indicated by arrow 109, side chains forming stabilizing interactions are indicated by arrow 110, and the peptide backbone is displayed as a ribbon and is indicated by arrow 111. Glu221 forms hydrogen bond interactions with the peptide backbone and electrostatic interactions with the helix dipole, stabilizing the N-terminus of helix B' and helix F', Trp109 forms π-π interactions with Phe238, stabilizing the packing of helix B' with helix G. In FIG. 5, two views of the active site cavity, which are rendered as a thin mesh (indicated by arrow 112) are shown. The side chains that contact the active site cavity are displayed as sticks. Atoms are represented according to element; O is indicated by arrow 113; N is indicated by arrow 114, and C is indicated by arrow 115 with the exception of the heme group which is indicated by arrow 116.

Although the electron density alone is unable to distinguish the orientation of the Asn side chain heteroatoms, additional hydrogen bonding interactions suggest that it is oriented as shown in FIG. 6, which depicts a wall-eyed stereo view of σA weighted 2|Fo|-|Fc| composite omit electron density maps contoured at 1σ and rendered within 1 Å of the heme and substrate for the coumarin. The substrate was omitted from the model used for the generation of the map. coumarin and methoxsalen are stabilized by hydrogen bonding with Asn297, which places the oxidized carbon 3.2±0.13 Å (coumarin) or 3.8±0.09 Å (methoxsalen) from the heme iron. The distances are shown as a dotted line and the values quoted for distances are the mean and standard deviation for the four molecules in the asymmetric unit. The peptide backbone is represented as a thin coil indicated by arrow 117, side chains are rendered as stick figures with the following representations for atoms; Carbons are indicated by arrow 118 for the protein or arrow 119 for substrates, oxygens are indicated by arrow 113, and nitrogens are indicated by arrow 114. The heme group is represented by arrow 107. In this conformation, the nitrogen from the $Asn_{297}$ side chain is able to donate a hydrogen bond to the ketal oxygen of the coumarin molecule, whereas the oxygen atom of the $Asn_{297}$ side chain is positioned to potentially accept two hydrogen bonds from the backbone nitrogen atom of residue 117 and a conserved water molecule normally found stabilizing the turn after the helix B'. The water molecule can accept a hydrogen bond from the peptide nitrogen of $F_{118}$ and donate a hydrogen bond to the carbonyl of $Y_{114}$ (FIG. 6). If the Asn297 side chain were rotated 180°, the nitrogen atoms from the $Asn_{297}$ side chain would clash with the backbone hydrogen atoms of residues 116 and 117.

Coumarin is positioned so that the 7' carbon, which is oxidized by the iron-oxo intermediate, resides 3.24±0.13 Å from the heme iron. Spectral titration studies with the purified CYP2A6 enzyme indicated that coumarin causes a type I spectral change which is consistent with displacement of water from its position as the sixth, axial ligand for the heme. The position of coumarin in the active site of CYP2A6 is consistent with the UV-visible spectroscopy, however the close distance between the coumarin molecule and the heme iron indicates that coumarin will have to move for the oxygen to bind and catalysis to occur. Typically, the distance of the heme iron atom to the atom that is oxidized is 4-5 Å based on a survey of P450-substrate complexes.

In addition to hydrogen bonding, there is a favorable interaction from the aromatic hydrogen of the coumarin molecule pointing directly into the ring system of $Phe_{107}$ depicted in FIG. 7. FIG. 7 is a depiction of a wall-eyed stereo view of σA weighted 2|Fo|-|Fc| composite omit electron density maps contoured at 1 σ and rendered within 1 Å of the heme and substrate for the methoxsalen. The substrate was omitted from the model used for the generation of the map. Coumarin and methoxsalen are stabilized by hydrogen bonding with $Asn_{297}$, which places the oxidized carbon 3.2±0.13 Å (coumarin) or 3.8±0.09 Å (methoxsalen) from the heme iron. The distances are shown as a dotted line and the values quoted for distances are the mean and standard deviation for the four molecules in the asymmetric unit. The peptide backbone is represented as a thin coil indicated by arrow 117, side chains are rendered as stick figures with the following representations for atoms; Carbons are indicated by arrow 118 for the protein or arrow 119 for substrates, oxygens are indicated by arrow 113, and nitrogens are indicated by arrow 114. The heme group is represented by arrow 107. Non-bonded potential energy calculations estimated the free energy gained from the aromatic interaction to be on the order of −1 to −2 kilocalories per mole, while the hydrogen bond between $Asn_{297}$ and coumarin is likely to contribute about −0.5 to −1.8 Kcal mol. Thus, the two interactions are likely to contribute to orienting the substrate for selective 7'-hydroxylation.

Methoxsalen is a mechanism based inhibitor of CYP2A6. Without being bound by a particular theory, the proposed mechanism for inactivation is indicated to be oxidation of the 5' carbon of methoxsalen to form a furanoepoxide followed by inactivation of CYP2A6. The location of the methoxsalen molecule is defined by the electron density in the active site as shown in FIG. 5. Although larger in size than coumarin, the ketal oxygen of methoxsalen also forms a hydrogen bond with the nitrogen atom of the $Asn_{297}$ side chain and aromatic hydrogens interact with the p-electron system of $Phe_{107}$. Although the 5' carbon is positioned 3.83±0.09 Å from the heme iron, the closest atom to the heme iron is the 1' oxygen, which resides only 3.33±0.08 Å from the heme iron. The slightly closer position of the oxygen molecule could limit the oxidation of the 5' position of methoxsalen, leading to uncoupling and generation of reactive oxygen species. Thus, this would support a model in which methoxsalen binding leads to significant uncoupling and subsequent inactivation of CYP2A6 by reactive oxygen species as proposed by Koenigs et al. (supra). No water molecules are evident in the active site, and as seen for coumarin, the binding of methoxsalen to the enzyme yields a type I spectral change.

In FIG. 9, a wall-eyed stereo view of the potential hydrogen bonding of Asn297 with coumarin (arrow 122), the polypeptide chain and a conserved water molecule bound in a turn following helix B' is depicted. The water molecule (arrow 123) is stabilized by accepting a hydrogen bond from the peptide nitrogen of F118 and donating hydrogen bonds to the carbonyl of Y114 and the side chain oxygen atom of N297. N297 is also stabilized by interactions with the hydrogen from the peptide nitrogen of V117. Hydrogen atoms are indicated by arrow 124, carbons are indicated by arrow 120 (coumarin) or arrow 118 (protein), oxygens are indicated by arrows 113 and nitrogens are indicated by arrow 114. The water molecule is displayed as a sphere (arrow 123), the side chains and heme group are rendered as stick figures.

In FIG. 10, a Wall-eyed stereo view of interactions between CYP2A6 and the heme prosthetic group. CYP2A6 differs from other cytochrome P450s by lacking the highly conserved WXXXR (SEQ ID NO: 5) motif, in which the W and R side chains hydrogen bond to the heme proprionate. CYP2A6 has an alanine (not shown) substitution for the tryptophan. The tryptophan side-chain of P450 2B4 at the equivalent position is shown for reference, A124W. Side chains donating hydrogen bonds to the heme proprionates are displayed as stick figures. The conserved cysteine residue (C439) that coordinates to the axial position of the heme iron is also shown. Carbons are indicated by arrow 125 (CYP2A6) or arrow 126 (cytochrome P450 2B4), nitrogens are indicated by arrow 114, oxygens are indicated by arrow 113, sulfur is indicated by arrow 127, and iron is indicated by arrow 128.

Example 8

This Example Illustrates Overall Fold and Comparison of CYP2A6 with Cytochrome P450 2C8

In this example, analysis of the structure of CYP2A6 based upon the data collected as described herein led us to conclude that CYP2A6 adopts an overall fold that is characteristic of other mammalian membrane associated P450s (FIG. 2), containing 16 α-helices, labeled A-L and 4 β-sheets, labeled numerically β1-β4. It differs from soluble prokaryotic cytochrome P450s by the addition of two helices, F' and G', located between helix F and G which are hydrophobic and thought to form part of the membrane interaction domain. In FIG. 2, helices are represented by arrow 100, and β-strands are represented by arrow 101. The cavity surface is rendered as a mesh and is indicated by arrow 102. The heme group is represented as a stick figure and is indicated by arrow 103.

The largest difference between the CYP2A6 structure and other experimentally determined structures of human drug metabolizing cytochrome P450s is the compact, hydrophobic nature of the active site cavity, which is bounded by the mesh surface shown in FIG. 2a. Substrate or solvent access channels are not evident. The active site volume is ~250 Å, which is significantly smaller than other human drug metabolizing P450s 2C8, 2C9 or 3A4 that exhibit volumes that are 4-6 fold larger. This reflects in part differences in the conformation of the peptide backbone that forms the outer surfaces of the active site cavity as shown in FIG. 2a, which compares Cα traces for CYP2A6 and cytochrome P450 2C8. These regions typically vary between family 2 drug metabolizing P450s and contribute to differences in the size and shape of the active site cavities. In contrast, the structural cores of the enzymes are highly similar as seen for CYP2A6 and cytochrome P450 2C8 (FIG. 2b). The comparison in FIG. 2 indicates that the pitch of the F and G helices that extend over the top of active site cavity above the heme is lower in CYP2A6 than in cytochrome P450 2C8. Additionally, the compact structure exhibits tight packing interactions between flexible portions of the cytochrome P450 structure, helix B to C and helix F to G with each other and the rest of the structure.

Hydrogen bonding and electrostatic interactions between $Glu_{221}$ on helix F' and the backbone nitrogens of residues 105 and 106 in the first turn of helix B' and with the helix dipole of helix B' stabilize this packing (FIG. 3a). In FIG. 3, regions that differ in position are depicted by arrow 104 for CYP2A6 and arrow 105 for cytochrome P450 2C8. Regions in which Cα positions overlay well are depicted by arrows 106. The heme group is represented as a stick figure and indicated by arrow 107 with the iron shown as a sphere. $Thr_{108}$ from helix B' and the backbone carbonyl of $Gly_{217}$ also interact through a bridging water molecule. A π-π stacking interaction between $Trp_{109}$ from helix B' and $Phe_{238}$ from helix G (FIG. 3a) also stabilizes the "active site" in a "closed" conformation. Additionally, there are significant aromatic interactions between the bulky side-chains of 5 phenylalanine residues ($Phe_{107}$, $Phe_{111}$, $Phe_{118}$, $Phe_{209}$ and $Phe_{480}$) that line the surface of the active site cavity above the heme, FIG. 3b. These residues contribute to the largely hydrophobic nature and small size of the CYP2A6 active site and are likely to stabilize the compact fold of the enzyme. The phenylalanine cluster lines the roof of the active site and may play an important role in stabilizing the binding of aromatic substrates within the active site. There are only two polar residues $Asn_{297}$ and $Thr_{305}$ (FIG. 3b). Thr305 is highly conserved in P450 active sites where it is thought to stabilize the interactions of reduced oxygen intermediates with a chain of water molecules that facilitate protonation of the reduced oxygen molecule to produce a compound I like oxo-heme intermediate.

Example 9

Crystallization of CYP2A6/(5-(pyridin-3-yl)furan-2-yl)methanamine and 4,4'-dipyridyldisulfide Complexes Crystallization of CYP2A6 was performed as described above. Data were collected from single crystals at Stanford Synchrotron Radiation Laboratory on beamline 9-1. All data were reduced and scaled in either HKL2000/Scalepack (Otwinowski, Z. and Minor, W. Processing of X-ray diffraction data collected in oscillation mode. Methods Enzymol. 1997, 276, 307-326.) or Mosflm/Scala (CCP The CCP4 suite: programs for protein crystallography. Acta Cryst. 1994, D50, 760-763). The data were phased initially by isomorphous replacement using the previously determined structure of CYP2A6dH, PDB:1Z10. The protein and inhibitor structures were fit to electron density maps using the computer program 0 (supra) and refined using CNS (supra). Data reduction and structure refinement statistics are presented in Table 7.

Example 10

Characterization of (5-(pyridin-3-yl)furan-2-yl) methanamine and 4,4'-dipyridyldisulfide CYP2A6 Inhibition (5-(pyridin-3-yl)furan-2-yl)methanamine, a known inhibitor of CYP2A6, and Aldrithiol-4™ (4,4'-dipyridyldisulfide), a potent inhibitor of CYP2A6, were compared. The activity of (5-(pyridin-3-yl)furan-2-yl)methanamine is described in Denton et al. 5-Substituted, 6-Substituted, and Unsubstituted 3-Heteroaromatic Pyridine Analogues of Nicotine as Selective Inhibitors of Cytochrome P-450 2A6. *J. Med. Chem.* 2005, 48, 224-239, incorporated herein by reference in its entirety.

The enzyme inhibitor complexes were crystallized using conditions similar to those employed previously for CYP2A6dH complexed with the substrate coumarin bound in the active site (supra). The data used for structure determination were collected from single crystals that diffracted to limiting resolutions of 2.05 Å and 1.65 Å in the $P2_1$ spacegroup for each of the (5-(pyridin-3-yl)furan-2-yl)methanamine and 4,4'-dipyridyldisulfide complexes (Table 7). Isomorphous replacement using the structure of CYP2A6dH (Table 2, Protein Data Bank Accession No. 1Z10) was used for initial phasing of the data followed by rounds of fitting and refinement. The position and orientation of each inhibitor in the active site was defined in sigma A weighted electron density maps. The results indicated that the (5-(pyridin-3-yl) furan-2-yl)methanamine and 4,4'-dipyridyldisulfide coordinated to the heme iron through the nitrogen atom of the primary amino group, respectively (FIG. 11). In FIG. 11, σA weighted 2|Fo|-|Fc| omit electron density maps contoured at 1 σ and rendered within 1.5 Å of the ligand for the complexes of CYP2A6 with (5-(Pyridin-3-yl)furan-2-yl)methanamine (left) and 4,4'-dipyridyldisulfide (right) bound in the active site are depicted. In each case, the substrate was omitted from the model used for the generation of the map. The dotted red lines indicate the potential for hydrogen bonding interactions with Asp297 or distance from the coordinating nitrogen to the heme iron.

The nitrogen of the amino group was located directly above the heme iron in the axial ligation position at distances of 2.27±0.02 Å for the primary amine. The structure of the CYP2A6 protein complexed with the primary amine was highly similar to that of the coumarin complex indicating that little reorganization of the enzyme was required for binding of (5-(pyridin-3-yl)furan-2-yl)methanamine. A comparison with the CYP2A6 complexes of coumarin and methoxsalen shows that (5-(pyridin-3-yl)furan-2-yl)methanamine, the identities of CYP2A6 residues that contact the substrates are the same. Additionally, most of the changes in contact residue positions are restricted to slight rearrangements of the phenylalanine residues to maximize orthogonal aromatic interactions with the inhibitors. The active site volume of the complexes also remains similar to that of the coumarin complex at ~240-275 Å.

This is in contrast to the complex of 4,4'-dipyridyldisulfide (FIG. 12). In FIG. 12, 4,4'-dipyridyldisulfide (Aldrithiol™ (ALD)) interactions with CYP2A6. The offset (shaded regions depicted behind the amino acids) in each of the amino acids depicted indicates the spatial differences as compared to the coumarin complex (coumarin is not depicted in the figure) . In order to accommodate 4,4'-dipyridyldisulfide, the side chain of $F_{209}$ moves away from the active site by ~3 Å relative to the coumarin complex to make room for the sulfur atoms of 4,4'-dipyridyldisulfide. This increases the active site volume to ~325 Å. The change in the active site provides clues as to how the protein can adapt to fit other, larger molecules in the active site. The pyridyl nitrogen of one ring is positioned 2.30±0.01 Å from the heme iron, and the bulky pryidyl ring also causes a repositioning of $Thr_{301}$ and an opening of helix I with a concomitant occupancy of the cleft by two water molecules. The other pyridyl nitrogen of 4,4'-dipyridyldisulfide is positioned 2.93±0.13 Å from the side-chain nitrogen of Asn297 and is in a position to accept a hydrogen bond as seen for the 3-pyridyl ring of (5-(pyridin-3-yl)furan-2-yl)methanamine. Thus, the changes in the active site maintain strong nitrogen coordination to the heme iron, a hydrogen bonding interaction with $Asn_{297}$, and orthogonal aromatic-aromatic interactions between the inhibitor and protein side-chains for all of these potent inhibitors. Without being bound by a particular theory, the high binding affinity for these relatively small molecules also likely stems from significant contributions of the hydrophobic effect arising from the displacement of water from the closed, hydrophobic active site cavity that exhibits extensive van der Waals interactions between the protein and inhibitor.

The results indicate that it is the side chain amino group of (5-(pyridin-3-yl) furan-2-yl)methanamine, that coordinates to the heme iron. This could reflect the importance of the hydrogen bonding and aromatic-aromatic interactions with the aromatic nitrogen of the pyridine ring relative to any inherent difference in the affinity of the amino versus the pyridine nitrogen for coordination to the heme iron.

Example 11

Graphics

Unless otherwise indicated, molecular graphics were generated in PyMOL (supra). All probe accessible cavity volumes were calculated with the program VOIDOO with a probe radius of 1.4 Å and grid spacing of 0.33 Å.

Other Aspects

The detailed description set-forth above is provided to aid those skilled in the art in practicing the present teachings. However, the teachings described and claimed herein is not to be limited in scope by the specific aspects herein disclosed because these aspects are intended as illustration of several aspects of the teachings. Any equivalent aspects are intended to be within the scope of this teachings. Indeed, various modifications of the teachings in addition to those shown and described herein will become apparent to those skilled in the art from the foregoing description which do not depart from the spirit or scope of the present inventive discovery. Such modifications are also intended to fall within the scope of the appended claims.

REFERENCES CITED

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present teachings. In particular, incorporated herein by reference in its entirety is: Yano J K, Hsu M H, Griffin K J, Stout C D, Johnson E F. Structures of human microsomal cytochrome P450 2A6 complexed with coumarin and methoxsalen. Nat. Struct. Mol. Biol. 2005 September; 12(9):822-3.

What is claimed is:

1. A crystalline complex comprising human cytochrome P450 2A6 in complex with a ligand: wherein the ligand is selected from the group consisting of 8-methoxypsoralen, coumarin, (5-(pyridin-3-yl)furan-2-yl)methanamine, and 4,4'-dipyridyldisulfide; wherein the human cytochrome P450 2A6 comprises a protein having the amino acid sequence set forth in SEQ ID NO: 2; and wherein the crystalline complex has space group $P2_1$, unit cell dimensions a=70.61±1.8 Å, b=157.59±1.8 Å, c=103.54±1.8 Å, β=92.25±0.50°.

2. A method of identifying a compound which interferes with an activity of human cytochrome P450 2A6, the method comprising:
   performing structure based drug design to identify a candidate inhibitor using a three-dimensional structure of human cytochrome P450 2A6 in complex with 8-methoxypsoralen, coumarin, (5-(pyridin-3-yl)furan-2-yl)methanamine, or 4,4'-dipyridyldisulfide which is defined by the atomic coordinates of Table 1, 2, 4 or 5, respectively, determined from an X-ray diffraction quality co-crystal of human cytochrome P450 2A6 protein in complex with 8-methoxypsoralen, coumarin, (5-(pyridin-3-yl)furan-2-yl)methanamine, or 4,4'-dipyridyldisulfide, wherein said protein comprises the amino acid sequence as set forth in SEQ ID NO: 2, and wherein said co-crystal has space group $P2_1$, unit cell dimensions a=70.61±1.8 Å, b=157.59±1.8 Å, c=103.54±1.8 Å, β=92.25±0.50°; and
   contacting the candidate inhibitor with the human cytochrome P450 2A6, wherein the inhibition of monooxygenase activity of the human cytochrome P450 2A6 by the candidate inhibitor identifies the candidate inhibitor as a compound which interferes with an activity of human cytochrome P450 2A6.

3. A method of screening for inhibiting activation of a procarcinogen in vitro, the method comprising:
   designing a candidate inhibitor of human cytochrome P450 2A6 by performing structure based drug design to identify a candidate inhibitor using a three-dimensional structure of human cytochrome P450 2A6 in complex with 8-methoxypsoralen, coumarin, (5-(pyridin-3-yl)furan-2-yl)methanamine, or 4,4'-dipyridyldisulfide which is defined by the atomic coordinates of Table 1, 2, 4 or 5, respectively, determined from an X-ray diffraction quality co-crystal of human cytochrome P450 2A6 protein in complex with 8-methoxypsoralen, coumarin, (5-(pyridin-3-yl)furan-2-yl)methanamine, or 4,4'-dipyridyldisulfide, wherein said protein comprises the amino acid sequence as set forth in SEQ ID NO: 2, and wherein said co-crystal has space group $P2_1$, unit cell dimensions a=70.61±1.8 Å, b=157.59±1.8 Å, c=103.54±1.8 Å, β=92.25±0.50°;
   contacting a sample comprising human cytochrome P450 2A6 with the candidate inhibitor; and
   selecting the candidates that inhibit activation of a procarcinogen in vitro.

4. The method of claim 3, wherein the procarcinogen is selected from the group consisting of N'-nitrosonornicotine (NNN), 4-(methylnitrosamino)-1-(3pyridyl)-1-butanone (NNK), and a combination thereof.

5. The method of claim 3, wherein the inhibitor is an antibody directed against the cytochrome P450 2A6.

6. A method of designing a compound which interferes with an activity of human cytochrome P450 2A6, the method comprising:
   providing on a digital computer a three-dimensional structure of human cytochrome P450 2A6 in complex with 8-methoxypsoralen, coumarin, (5-(pyridin-3-yl)furan-2-yl)methanamine, or 4,4'-dipyridyldisulfide which is defined by the atomic coordinates of Table 1, 2, 4 or 5, respectively, determined from an X-ray diffraction quality co-crystal of human cytochrome P450 2A6 protein in complex with 8-methoxypsoralen, coumarin, (5-(pyridin-3-yl)furan-2-yl)methanamine, or 4,4'-dipyridyldisulfide, wherein said protein comprises the amino acid sequence as set forth in SEQ ID NO: 2, and wherein said co-crystal has space group $P2_1$, unit cell dimensions a=70.61±1.8 Å, b=157.59±1.8 Å, c=103.54±1.8 Å, β=92.25±0.50°; and
   employing software comprised by the digital computer to design the compound which is predicted to bind to the human cytochrome P450 2A6.

7. The method of claim 6, further comprising:
   synthesizing the compound; and
   evaluating the compound for an ability to interfere with a monooxygenase activity of the human cytochrome P450 2A6.

8. The method of claim 6, wherein the compound is designed by computational interaction with reference to a three dimensional site of the structure of cytochrome P450 2A6 in complex with the ligand, wherein the three dimensional site comprises a plurality of cytochrome P450 2A6 amino acids, numbered with reference to the sequence of SEQ ID NO: 1, selected from the group consisting of Phe107, Phe111, Phe118, Phe209, Phe480, Val117, Asn297, Ile 300, Gly301, Thr305, Ile366, Leu370, and combinations thereof.

9. The method of claim 6, further comprising employing software comprised by the digital computer to design a compound which is predicted not to bind to a cytochrome P450 other than human cytochrome P450 2A6.

10. The method of claim 9, wherein the cytochrome P450 other than human cytochrome P450 2A6 is a cytochrome P450 selected from the group consisting of cytochrome P450 2C8, cytochrome P450 2C9, cytochrome P450 3A4, and combinations thereof.

* * * * *

SEQUENCE LISTING

<160> NUMBER OF SEQ ID NOS: 5

<210> SEQ ID NO 1
<211> LENGTH: 494
<212> TYPE: PRT
<213> ORGANISM: Homo sapiens

<400> SEQUENCE: 1

Met Leu Ala Ser Gly Met Leu Val Ala Leu Leu Val Cys Leu Thr
1               5                   10                  15

Val Met Val Leu Met Ser Val Trp Gln Gln Arg Lys Ser Lys Gly Lys
            20                  25                  30

Leu Pro Pro Gly Pro Thr Pro Leu Pro Phe Ile Gly Asn Tyr Leu Gln
            35                  40                  45

Leu Asn Thr Glu Gln Met Tyr Asn Ser Leu Met Lys Ile Ser Glu Arg
        50                  55                  60

Tyr Gly Pro Val Phe Thr Ile His Leu Gly Pro Arg Arg Val Val Val
65                  70                  75                  80

Leu Cys Gly His Asp Ala Val Arg Glu Ala Leu Val Asp Gln Ala Glu
            85                  90                  95

Glu Phe Ser Gly Arg Gly Glu Gln Ala Thr Phe Asp Trp Val Phe Lys
            100                 105                 110

Gly Tyr Gly Val Val Phe Ser Asn Gly Glu Arg Ala Lys Gln Leu Arg
            115                 120                 125

Arg Phe Ser Ile Ala Thr Leu Arg Asp Phe Gly Val Gly Lys Arg Gly
        130                 135                 140

Ile Glu Glu Arg Ile Gln Glu Glu Ala Gly Phe Leu Ile Asp Ala Leu
145                 150                 155                 160

Arg Gly Thr Gly Gly Ala Asn Ile Asp Pro Thr Phe Phe Leu Ser Arg
            165                 170                 175

Thr Val Ser Asn Val Ile Ser Ser Ile Val Phe Gly Asp Arg Phe Asp
            180                 185                 190

Tyr Lys Asp Lys Glu Phe Leu Ser Leu Leu Arg Met Met Leu Gly Ile
            195                 200                 205

Phe Gln Phe Thr Ser Thr Ser Thr Gly Gln Leu Tyr Glu Met Phe Ser
        210                 215                 220

Ser Val Met Lys His Leu Pro Gly Pro Gln Gln Ala Phe Gln Leu
225                 230                 235                 240

Leu Gln Gly Leu Glu Asp Phe Ile Ala Lys Lys Val Glu His Asn Gln
            245                 250                 255

Arg Thr Leu Asp Pro Asn Ser Pro Arg Asp Phe Ile Asp Ser Phe Leu
            260                 265                 270

Ile Arg Met Gln Glu Glu Glu Lys Asn Pro Asn Thr Glu Phe Tyr Leu
        275                 280                 285

Lys Asn Leu Val Met Thr Thr Leu Asn Leu Phe Ile Gly Gly Thr Glu
    290                 295                 300

Thr Val Ser Thr Thr Leu Arg Tyr Gly Phe Leu Leu Leu Met Lys His
305                 310                 315                 320

Pro Glu Val Glu Ala Lys Val His Glu Glu Ile Asp Arg Val Ile Gly
            325                 330                 335

Lys Asn Arg Gln Pro Lys Phe Glu Asp Arg Ala Lys Met Pro Tyr Met
            340                 345                 350

Glu Ala Val Ile His Glu Ile Gln Arg Phe Gly Asp Val Ile Pro Met
            355                 360                 365

```
Ser Leu Ala Arg Arg Val Lys Lys Asp Thr Lys Phe Arg Asp Phe
    370                 375                 380

Leu Pro Lys Gly Thr Glu Val Tyr Pro Met Leu Gly Ser Val Leu Arg
385                 390                 395                 400

Asp Pro Ser Phe Phe Ser Asn Pro Gln Asp Phe Asn Pro Gln His Phe
                405                 410                 415

Leu Asn Glu Lys Gly Gln Phe Lys Lys Ser Asp Ala Phe Val Pro Phe
                420                 425                 430

Ser Ile Gly Lys Arg Asn Cys Phe Gly Glu Gly Leu Ala Arg Met Glu
                435                 440                 445

Leu Phe Leu Phe Phe Thr Thr Val Met Gln Asn Phe Arg Leu Lys Ser
450                 455                 460

Ser Gln Ser Pro Lys Asp Ile Asp Val Ser Pro Lys His Val Gly Phe
465                 470                 475                 480

Ala Thr Ile Pro Arg Asn Tyr Thr Met Ser Phe Leu Pro Arg
                485                 490

<210> SEQ ID NO 2
<211> LENGTH: 466
<212> TYPE: PRT
<213> ORGANISM: Homo sapiens

<400> SEQUENCE: 2

Ser Lys Gly Lys Leu Pro Pro Gly Pro Thr Pro Leu Pro Phe Ile Gly
1               5                   10                  15

Asn Tyr Leu Gln Leu Asn Thr Glu Gln Met Tyr Asn Ser Leu Met Lys
                20                  25                  30

Ile Ser Glu Arg Tyr Gly Pro Val Phe Thr Ile His Leu Gly Pro Arg
            35                  40                  45

Arg Val Val Val Leu Cys Gly His Asp Ala Val Arg Glu Ala Leu Val
        50                  55                  60

Asp Gln Ala Glu Glu Phe Ser Gly Arg Gly Glu Gln Ala Thr Phe Asp
65                  70                  75                  80

Trp Val Phe Lys Gly Tyr Gly Val Val Phe Ser Asn Gly Glu Arg Ala
                85                  90                  95

Lys Gln Leu Arg Arg Phe Ser Ile Ala Thr Leu Arg Asp Phe Gly Val
                100                 105                 110

Gly Lys Arg Gly Ile Glu Glu Arg Ile Gln Glu Glu Ala Gly Phe Leu
            115                 120                 125

Ile Asp Ala Leu Arg Gly Thr Gly Gly Ala Asn Ile Asp Pro Thr Phe
130                 135                 140

Phe Leu Ser Arg Thr Val Ser Asn Val Ile Ser Ser Ile Val Phe Gly
145                 150                 155                 160

Asp Arg Phe Asp Tyr Lys Asp Lys Glu Phe Leu Ser Leu Leu Arg Met
                165                 170                 175

Met Leu Gly Ile Phe Gln Phe Thr Ser Thr Ser Thr Gly Gln Leu Tyr
            180                 185                 190

Glu Met Phe Ser Ser Val Met Lys His Leu Pro Gly Pro Gln Gln Gln
        195                 200                 205

Ala Phe Gln Leu Leu Gln Gly Leu Glu Asp Phe Ile Ala Lys Lys Val
    210                 215                 220

Glu His Asn Gln Arg Thr Leu Asp Pro Asn Ser Pro Arg Asp Phe Ile
225                 230                 235                 240

Asp Ser Phe Leu Ile Arg Met Gln Glu Glu Glu Lys Asn Pro Asn Thr
                245                 250                 255
```

```
Glu Phe Thr Leu Lys Asn Leu Val Met Thr Thr Leu Asn Leu Phe Ile
        260                 265                 270

Gly Gly Thr Glu Thr Val Ser Thr Thr Leu Arg Tyr Gly Phe Leu Leu
    275                 280                 285

Leu Met Lys His Pro Glu Val Glu Ala Lys Val His Glu Glu Ile Asp
    290                 295                 300

Arg Val Ile Gly Lys Asn Arg Gln Pro Lys Phe Glu Asp Arg Ala Lys
305                 310                 315                 320

Met Pro Tyr Met Glu Ala Val Ile His Glu Ile Gln Arg Phe Gly Asp
                325                 330                 335

Val Ile Pro Met Ser Leu Ala Arg Arg Val Lys Lys Asp Thr Lys Phe
            340                 345                 350

Arg Asp Phe Phe Leu Pro Lys Gly Thr Glu Val Tyr Pro Met Leu Gly
        355                 360                 365

Ser Val Leu Arg Asp Pro Ser Phe Phe Ser Asn Pro Gln Asp Phe Asn
    370                 375                 380

Pro Gln His Phe Leu Asn Glu Lys Gly Gln Phe Lys Lys Ser Asp Ala
385                 390                 395                 400

Phe Val Pro Phe Ser Ile Gly Lys Arg Asn Cys Phe Gly Glu Gly Leu
                405                 410                 415

Ala Arg Met Glu Leu Phe Leu Phe Phe Thr Thr Val Met Gln Asn Phe
            420                 425                 430

Arg Leu Lys Ser Ser Gln Ser Pro Lys Asp Ile Asp Val Ser Pro Lys
        435                 440                 445

His Val Gly Phe Ala Thr Ile Pro Arg Asn Tyr Thr Met Ser Phe Leu
    450                 455                 460

Pro Arg
465

<210> SEQ ID NO 3
<211> LENGTH: 476
<212> TYPE: PRT
<213> ORGANISM: Homo sapiens

<400> SEQUENCE: 3

Met Ala Lys Lys Thr Ser Ser Lys Gly Lys Leu Pro Pro Gly Pro Thr
1               5                   10                  15

Pro Leu Pro Phe Ile Gly Asn Tyr Leu Gln Leu Asn Thr Glu Gln Met
            20                  25                  30

Tyr Asn Ser Leu Met Lys Ile Ser Glu Arg Tyr Gly Pro Val Phe Thr
        35                  40                  45

Ile His Leu Gly Pro Arg Arg Val Val Val Leu Cys Gly His Asp Ala
    50                  55                  60

Val Arg Glu Ala Leu Val Asp Gln Ala Glu Glu Phe Ser Gly Arg Gly
65                  70                  75                  80

Glu Gln Ala Thr Phe Asp Trp Val Phe Lys Gly Tyr Gly Val Val Phe
                85                  90                  95

Ser Asn Gly Glu Arg Ala Lys Gln Leu Arg Arg Phe Ser Ile Ala Thr
            100                 105                 110

Leu Arg Asp Phe Gly Val Gly Lys Arg Gly Ile Glu Glu Arg Ile Gln
        115                 120                 125

Glu Glu Ala Gly Phe Leu Ile Asp Ala Leu Arg Gly Thr Gly Gly Ala
    130                 135                 140

Asn Ile Asp Pro Thr Phe Phe Leu Ser Arg Thr Val Ser Asn Val Ile
145                 150                 155                 160
```

```
Ser Ser Ile Val Phe Gly Asp Arg Phe Asp Tyr Lys Asp Lys Glu Phe
            165                 170                 175

Leu Ser Leu Leu Arg Met Met Leu Gly Ile Phe Gln Phe Thr Ser Thr
            180                 185                 190

Ser Thr Gly Gln Leu Tyr Glu Met Phe Ser Ser Val Met Lys His Leu
        195                 200                 205

Pro Gly Pro Gln Gln Gln Ala Phe Gln Leu Leu Gln Gly Leu Glu Asp
    210                 215                 220

Phe Ile Ala Lys Lys Val Glu His Asn Gln Arg Thr Leu Asp Pro Asn
225                 230                 235                 240

Ser Pro Arg Asp Phe Ile Asp Ser Phe Leu Ile Arg Met Gln Glu Glu
            245                 250                 255

Glu Lys Asn Pro Asn Thr Glu Phe Tyr Leu Lys Asn Leu Val Met Thr
            260                 265                 270

Thr Leu Asn Leu Phe Ile Gly Gly Thr Glu Thr Val Ser Thr Thr Leu
            275                 280                 285

Arg Tyr Gly Phe Leu Leu Leu Met Lys His Pro Glu Val Glu Ala Lys
        290                 295                 300

Val His Glu Glu Ile Asp Arg Val Ile Gly Lys Asn Arg Gln Pro Lys
305                 310                 315                 320

Phe Glu Asp Arg Ala Lys Met Pro Tyr Met Glu Ala Val Ile His Glu
            325                 330                 335

Ile Gln Arg Phe Gly Asp Val Ile Pro Met Ser Leu Ala Arg Arg Val
            340                 345                 350

Lys Lys Asp Thr Lys Phe Arg Asp Phe Phe Leu Pro Lys Gly Thr Glu
        355                 360                 365

Val Tyr Pro Met Leu Gly Ser Val Leu Arg Asp Pro Ser Phe Phe Ser
    370                 375                 380

Asn Pro Gln Asp Phe Asn Pro Gln His Phe Leu Asn Glu Lys Gly Gln
385                 390                 395                 400

Phe Lys Lys Ser Asp Ala Phe Val Pro Phe Ser Ile Gly Lys Arg Asn
            405                 410                 415

Cys Phe Gly Glu Gly Leu Ala Arg Met Glu Leu Phe Leu Phe Phe Thr
            420                 425                 430

Thr Val Met Glu Asn Phe Arg Leu Lys Ser Ser Gln Ser Pro Lys Asp
        435                 440                 445

Ile Asp Val Ser Pro Lys His Val Gly Phe Ala Thr Ile Pro Arg Asn
    450                 455                 460

Tyr Thr Met Ser Phe Leu Pro Arg His His His
465                 470                 475

<210> SEQ ID NO 4
<211> LENGTH: 6
<212> TYPE: PRT
<213> ORGANISM: Artificial Sequence
<220> FEATURE:
<223> OTHER INFORMATION: Synthesized in laboratory.

<400> SEQUENCE: 4

Met Ala Lys Lys Thr Ser
1               5

<210> SEQ ID NO 5
<211> LENGTH: 5
<212> TYPE: PRT
<213> ORGANISM: Homo sapiens
<220> FEATURE:
```

```
<221> NAME/KEY: MISC_FEATURE
<222> LOCATION: (2)..(4)
<223> OTHER INFORMATION: Xaa in Heme Binding Motif can be any amino
      acid.

<400> SEQUENCE: 5

Trp Xaa Xaa Xaa Arg
1               5
```